US011253155B2

(12) United States Patent
Arai et al.

(10) Patent No.: US 11,253,155 B2
(45) Date of Patent: Feb. 22, 2022

(54) BRAIN ACTIVITY ESTIMATION DEVICE

(71) Applicants: DAIKIN INDUSTRIES, LTD., Osaka (JP); TOKYO INSTITUTE OF TECHNOLOGY, Tokyo (JP)

(72) Inventors: Junichiro Arai, Osaka (JP); Yasunori Kotani, Tokyo (JP); Yoshimi Ohgami, Tokyo (JP); Taro Tomatsu, Tokyo (JP)

(73) Assignees: Daikin Industries, Ltd., Osaka (JP); TOKYO INSTITUTE OF TECHNOLOGY, Tokyo (JP)

( * ) Notice: Subject to any disclaimer, the term of this patent is extended or adjusted under 35 U.S.C. 154(b) by 149 days.

(21) Appl. No.: 15/735,104

(22) PCT Filed: Jun. 13, 2016

(86) PCT No.: PCT/JP2016/067578
§ 371 (c)(1),
(2) Date: Dec. 8, 2017

(87) PCT Pub. No.: WO2016/199940
PCT Pub. Date: Dec. 15, 2016

(65) Prior Publication Data
US 2018/0168451 A1    Jun. 21, 2018

(30) Foreign Application Priority Data

Jun. 12, 2015  (JP) .............................. JP2015-119350

(51) Int. Cl.
*G06K 9/00*    (2006.01)
*A61B 5/00*    (2006.01)
(Continued)

(52) U.S. Cl.
CPC .............. *A61B 5/0042* (2013.01); *A61B 5/00* (2013.01); *A61B 5/0064* (2013.01);
(Continued)

(58) Field of Classification Search
CPC ... A61B 5/0042; A61B 5/7246; A61B 5/4064; A61B 5/015; A61B 5/0075; A61B 5/0064; A61B 5/055; A61B 5/0476; A61B 5/00
See application file for complete search history.

(56) References Cited

U.S. PATENT DOCUMENTS 9,204,836 B2 * 12/2015 Bender .................. G16H 40/67
10,289,898 B2 * 5/2019 el Kaliouby ........... A61B 5/165
(Continued)

FOREIGN PATENT DOCUMENTS

CN    104545864 A    4/2015
JP    2013-176406 A  9/2013
(Continued)

OTHER PUBLICATIONS

European Search Report of corresponding EP Application No. 16 80 7643.8 dated Jan. 18, 2019.
(Continued)

*Primary Examiner* — Tom Y Lu
(74) *Attorney, Agent, or Firm* — Global IP Counselors, LLP

(57) ABSTRACT

A brain activity estimation device includes a brain activity estimation portion. The brain activity estimation portion includes a blood-circulation-amount calculating unit and an estimation unit. The blood-circulation-amount calculating unit is configured to calculate time-series blood-circulation-amount data on a facial surface of a human based on RGB data of photographed image data on the facial surface acquired in time series. The RGB data is obtained by conducting RGB processing on the photographed image data. The RGB processing includes decomposing the photographed image data into three color components composed of an R component, a G component and a B component. The estimation unit is configured to estimate brain activity of the
(Continued)

human based on a plurality of decomposition components obtained by decomposing the blood-circulation-amount data by singular value decomposition, principal component analysis, or independent component analysis.

18 Claims, 15 Drawing Sheets

(51) Int. Cl.
*A61B 5/01* (2006.01)
*A61B 5/369* (2021.01)
*A61B 5/055* (2006.01)

(52) U.S. Cl.
CPC ............ *A61B 5/0075* (2013.01); *A61B 5/015* (2013.01); *A61B 5/4064* (2013.01); *A61B 5/7246* (2013.01); *A61B 5/055* (2013.01); *A61B 5/369* (2021.01)

(56) References Cited

U.S. PATENT DOCUMENTS

| | | |
|---|---|---|
| 2009/0080730 A1 | 3/2009 | Pavlidis |
| 2011/0251493 A1 | 10/2011 | Poh et al. |
| 2014/0121540 A1 | 5/2014 | Raskin |
| 2015/0148687 A1* | 5/2015 | Kitajima ............ A61B 5/02427 600/477 |
| 2018/0168451 A1 | 6/2018 | Arai et al. |

FOREIGN PATENT DOCUMENTS

| | | |
|---|---|---|
| JP | 2017-773 A | 1/2017 |
| WO | 2014068436 A1 | 5/2014 |
| WO | 2014/145204 A1 | 9/2014 |

OTHER PUBLICATIONS

International Search Report of corresponding PCT Application No. PCT/JP2016/067578 dated Sep. 6, 2016.
International Preliminary Report of corresponding PCT Application No. PCT/JP2016/067578 dated Dec. 21, 2017.

* cited by examiner

BRAIN ACTIVITY ESTIMATION DEVICE

CROSS-REFERENCE TO RELATED APPLICATIONS

This U.S. National stage application claims priority under 35 U.S.C. § 119(a) to Japanese Patent Application No. 2015-119350, filed in Japan on Jun. 12, 2015, the entire contents of which are hereby incorporated herein by reference.

TECHNICAL FIELD

The present invention relates to a brain activity estimation device for estimating human brain activity.

BACKGROUND ART

There have been attempts in the prior art to estimate human brain activity utilizing data that has been detected by electroencephalography (EEG), functional magnetic resonance imaging (fMRI), or near infrared spectroscopy (NIRS), such as is disclosed in Japanese Laid-open Patent Publication 2013-176406.

SUMMARY

Technical Problem

However, in cases where the electroencephalography or the near infrared spectroscopy is adopted as a detection method, an electrode or probe which requires preprocessing needs to be applied to the test subject. In cases where the functional magnetic resonance imaging is adopted as a detection method, measuring can only be carried out in an MRI room. That is, in cases where any one of the electroencephalography, the functional magnetic resonance imaging, and the near infrared spectroscopy is adopted as a detection method to detect data, there are problems, such as the complexity of necessary operations to be conducted in the preparatory stage or the limitations of conditions during detection.

Accordingly, it is an object of the present invention to provide a brain activity estimation device that can easily estimate human brain activity.

Solution to Problem

A brain activity estimation device according to a first aspect of the present invention includes a brain activity estimation means that has a blood-circulation-amount calculating unit and an estimation unit. The blood-circulation-amount calculating unit calculates time-series blood-circulation-amount data on a facial surface of a human based on RGB data of photographed image data on the facial surface acquired in time series. The RGB data is obtained by conducting RGB processing on the photographed image data. The RGB processing is to decompose the photographed image data into three color components composed of an R component, a G component and a B component. The estimation unit estimates brain activity of the human based on a plurality of components obtained by decomposing the blood-circulation-amount data by singular value decomposition, principal component analysis, or independent component analysis.

With the brain activity estimation device according to the first aspect of the present invention, the human brain activity can be estimated based on the time-series photographed image data on the facial surface. Therefore, the human brain activity can be easily estimated, compared to a case where a conventional detection method is used, such as the electroencephalography, the functional magnetic resonance imaging, and the near infrared spectroscopy.

A brain activity estimation device according to a second aspect of the present invention is the brain activity estimation device according to the first aspect of the present invention wherein the brain activity estimation means extracts a component as a determination component from the plurality of components. The determination component has a component waveform with an amplitude that has a correlation with changes of the brain at a brain resting time and a brain activated time. Further, the brain activity estimation means estimates the brain activity of the human based on the determination component. In the brain activity estimation device, the component that has the correlation with rest/activation of the brain is extracted as the determination component for estimating the human brain activity, from the plurality of components. Thus, the brain activity can be estimated from the component that is expected to have a high relevance with the human brain activity.

A brain activity estimation device according to a third aspect of the present invention is the brain activity estimation device according to the second aspect of the present invention wherein the photographed image data includes data in a period of time during which a brain function activation task is being given to the human. The brain activity estimation means evaluates whether the plurality of components has the correlation, with the brain resting time being a period of time during which no brain function activation task is given to the human and with the brain activated time being a period of time during which the brain function activation task is given to the human. Further, the brain activity estimation means extracts the component that is evaluated to have the correlation, as the determination component from the plurality of components. In the brain activity estimation device, the presence or absence of the brain function activation task actually given to a human brings the human brain into the activated state or the resting state. Based on this, the correlation is evaluated and the determination component is extracted. Thus, the probability of extraction of the component, which is less related to the human brain activity, as an extraction component from the plurality of components, can be reduced.

A brain activity estimation device according to a fourth aspect of the present invention is the brain activity estimation device according to any one of the first to third aspects of the present invention wherein the blood-circulation-amount data is acquired from a paranasal sinus peripheral region and/or a forehead of the facial surface of the human.

Here, the brain has a mechanism called "Selective Brain Cooling System" to cool the brain independently of the body temperature. The selective brain cooling system is known to discharge heat generated by the brain activity using the peripheral region of the paranasal sinus and the forehead.

In the brain activity estimation device according to the fourth aspect of the present invention, the human brain activity is estimated based on the time-series blood-circulation-amount data at the paranasal sinus and/or the forehead where the brain activity is expected to be reflected. Since the facial skin temperature is considered to be proportional to the blood-circulation-amount of the facial surface, the brain activity estimation device can estimate the human brain activity with high accuracy.

A brain activity estimation device according to a fifth aspect of the present invention is the brain activity estimation device according to any one of the first to fourth aspects of the present invention wherein the brain activity estimation means includes a conversion unit. The conversion unit converts the RGB data obtained from the acquired photographed image data every predetermined time into relative RGB data. The blood-circulation-amount calculating unit calculates time-series blood-circulation-amount data on the facial surface based on the relative RGB data.

In a case where the photographed image data is obtained by photographing the human facial surface using the photographing device, such as a camera, for example, if sunlight or the like hits the face during photographing, the light is reflected by the face. The reflected light occasionally enters a lens of the photographing device in some cases. As a result, the photographed image data would have the reflected light recorded therein. Here, in the RGB data, a change in brightness based on the blood-circulation-amount of the face is smaller than a change in brightness based on the reflected light. Because of this, if the blood-circulation-amount is calculated based on the RGB data obtained from the photographed image data with the reflected light recorded therein, the blood-circulation-amount might be determined erroneously.

In the brain activity estimation device according to the fifth aspect of the present invention, the time-series blood-circulation-amount data is calculated based on the relative RGB data obtained from the acquired photographed image data at every predetermined time. Because of this, the relative change in the blood-circulation-amount of the facial surface can be captured every predetermined time. Thus, the erroneous determination of the blood-circulation-amount due to the external factor unrelated to the brain activity can be reduced.

A brain activity estimation device according to a sixth aspect of the present invention is the brain activity estimation device according to any one of the first to fifth aspects of the present invention wherein the brain activity estimation device further includes image data acquisition means and an RGB processing unit. The image data acquisition means acquires the photographed image data on the facial surface of the human in time series. The RGB processing unit conducts the RGB processing on the photographed image data: the RGB processing decomposes the photographed image data into three color components composed of the R component, the G component, and the B component.

In the brain activity estimation device according to the sixth aspect of the present invention, the human brain activity is estimated based on the time-series photographed image data on the human facial surface acquired by the image data acquisition means. Thus, with the brain activity estimation device, the human brain activity can be estimated based on the time-series photographed image data on the facial surface without attaching any sensors that requires preprocessing before attachment, such as brain wave electrodes and probes. Therefore, the human brain activity can be easily estimated, compared to the case where the conventional detection method is used, such as the electroencephalography, the functional magnetic resonance imaging, and the near infrared spectroscopy.

A brain activity estimation device according to a seventh aspect of the present invention is the brain activity estimation device according to any one of the first to sixth aspects of the present invention wherein the photographed image data is acquired by a camera that photographs an image in a visible light region. The brain activity estimation device can acquire the photographed image data by a common camera, which can simplify the device. Thus, the human brain activity can be estimated even more easily.

A brain activity estimation device according to an eighth aspect of the present invention is the brain activity estimation device according to any one of the first to seventh aspects of the present invention wherein the blood-circulation-amount calculating unit calculates the blood-circulation-amount data on the facial surface by mainly using the R component of each of pixels included in the RGB data. The brain activity estimation device mainly uses the R components, thereby making it possible to satisfactorily calculate the blood-circulation-amount.

A brain activity estimation device according to a ninth aspect of the present invention is the brain activity estimation device according to any one of the first to sixth aspects of the present invention wherein the photographed image data is acquired by an infrared camera. Therefore, the brain activity estimation device can obtain the photographed image data regardless of the brightness of external environment.

Advantageous Effects of Invention

With the brain activity estimation device according to the first aspect of the present invention, the human brain activity can be easily estimated.

With the brain activity estimation device according to the second aspect of the present invention, the brain activity can be estimated from the component that is expected to have a high relevance with the human brain activity.

With the brain activity estimation device according to the third aspect of the present invention, the probability of extraction of the component which is less related to the human brain activity as the extraction component from the plurality of components can be reduced.

With the brain activity estimation device according to the fourth aspect of the present invention, the human brain activity can be estimated with high accuracy.

With the brain activity estimation device according to the fifth aspect of the present invention, the erroneous determination of the blood-circulation-amount due to the external factor not related to the brain activity can be reduced.

With the brain activity estimation device according to the sixth aspect of the present invention, the human brain activity can be easily estimated.

With the brain activity estimation device according to the seventh aspect of the present invention, the photographed image data can be acquired by the common camera, thereby making it possible to easily estimate the human brain activity.

With the brain activity estimation device according to the eighth aspect of the present invention, the R component is mainly used, thereby making it possible to satisfactorily calculate the blood-circulation-amount.

With the brain activity estimation device according to the ninth aspect of the present invention, the photographed image data is acquired by the infrared camera, thereby making it possible to estimate the human brain activity regardless of the brightness of external environment.

DESCRIPTION OF EMBODIMENTS

Figure 1B:
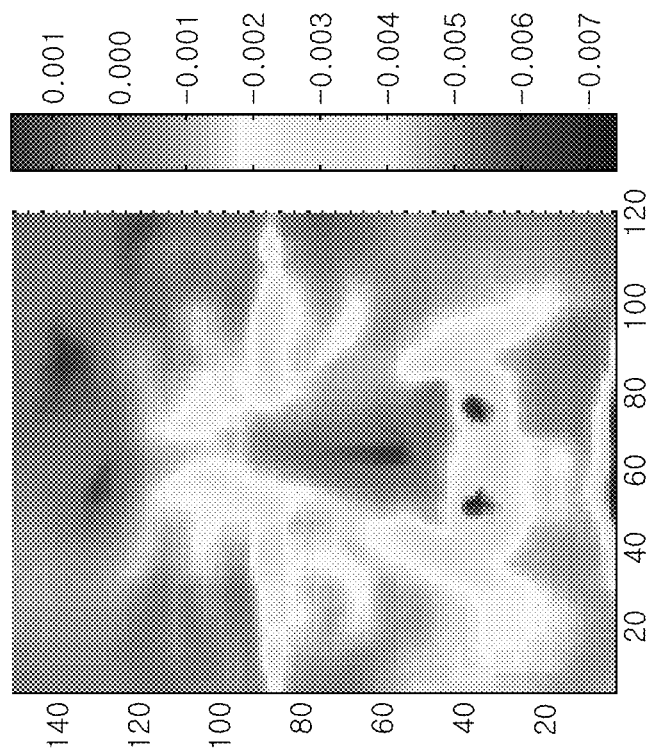
FIG. 1B is a diagram showing an example of the distribution of the blood-circulation-amount.

Before describing the embodiments of the present invention, the findings made by the inventors that served as an important foundation for the inventors to contrive the present invention will be described first.

(1) SUMMARY OF FINDINGS MADE BY THE INVENTORS

It is known that human's intellectual activity (cognitive activity and the like) and emotional activity (activity such as pleasure/displeasure) are reflected in a human brain activity. Attempts to estimate the human brain activity have been made in the past, but in most cases, data detected by any method of electroencephalography, functional magnetic resonance imaging, and near infrared spectroscopy was utilized.

In cases where, for example, the electroencephalography is adopted as a detection method, it is necessary to attach brain wave electrodes to a test subject. Since it is moreover necessary to reduce resistance between the skin and the electrodes when the brain wave electrodes are attached, a procedure such as a process to abrade the skin or an application of a paste to the electrodes needs to be carried out. In cases where the functional magnetic resonance imaging is adopted, there are restrictions on measurement conditions, such as the impossibility of measurement at any location other than an MRI room and the prohibition of bringing metal to a measurement room. In cases where the near infrared spectroscopy is adopted, a probe needs to be attached to the test subject. However, wearing the probe for a long time would make the test subject feel pain, and the probe cannot occasionally perform detection with accuracy depending on a contact condition between hair of the test subject and the probe. In this way, when using conventional detection methods to measure the human brain activity, a significant burden is imposed on the test subject, specifically, preprocessing is needed to attach the brain wave electrode, the probe, etc., or the measurement conditions are limited.

Accordingly, there is a need to develop an approach that can easily estimate the human brain activity while reducing the burden on the test subject.

The inventors have found that the human brain activity can be estimated in the ways below (see Japanese Patent Application No. 2014-177276). Specifically, facial skin temperature data including a human face skin temperature is acquired in time series using a measurement device capable of measuring temperature data and detection-part position data (coordinate data) such as a thermography device. The acquired data is decomposed into a plurality of components by a singular value decomposition method, a principal component analysis method, or an independent component analysis method. Then, the plurality of decomposed components is analyzed.

Meanwhile, it is generally said that the measurement device employed in the electroencephalography method costs several million Japanese yen; the equipment used in the functional magnetic resonance imaging significantly costs a huge scale of several hundred million Japanese yen; and the measurement device employed in the near infrared spectroscopy also costs several tens of millions of Japanese yen. It is said that even when the human brain activity is estimated based on the facial skin temperature data acquired by using the thermography device, the thermography device generally costs several tens of thousands of Japanese yen. For this reason, it is desirable to develop an approach that enables estimation of the human brain activity at a lower cost.

Thus, the inventors have thought that if the human brain activity can be estimated based on the facial skin temperature data acquired by measuring the human's facial skin temperature, the human brain activity can be estimated based on a blood-circulation-amount of the facial surface, because the blood-circulation-amount is considered to be proportional to the facial skin temperature. A blood-circulation-state of the facial surface, i.e., the blood-circulation-amount of the facial surface can be estimated from RGB data obtained by using the photographed image data on the human's facial surface. Further, the photographed image data on the human's facial surface can be acquired in time series at a relatively low cost without attaching any sensors that require preprocessing.

Here, it is known that the human facial skin temperature varies due to the influence of various factors, such as the outside air temperature and/or autonomic nerve activities. Thus, in an attempt to estimate the brain activity based on the blood-circulation-amount of the facial surface, which is considered to be proportional to the facial skin temperature, it is thought to be very difficult to determine whether or not the acquired facial skin temperature reflects only the brain activity.

As a result of painstaking research, the inventors of the present application have found that it is possible to identify a component exhibiting a change in the blood-circulation-amount of the facial surface that reflects the brain activity, i.e., a change in the RGB data on the facial surface in an approach in which time-series data on the blood-circulation-amount of the facial surface that is calculated based on the RGB data obtained from time-series photographed image data on the facial surface is decomposed into the plurality of components using the singular value decomposition method, the principal component analysis method, or the independent component analysis method, and then, the plurality of decomposed components is analyzed. In other words, it has been revealed that, in an attempt to estimate the human brain activity based on the photographed image data on the facial surface, it is effective to decompose the blood-circulation-amount data based on the RGB data obtained from the time-series photographed image data on the facial surface into the plurality of components by the singular value decomposition method, the principal component analysis method, or the independent component analysis method. By focusing on this point, the inventors have conceived of the present invention that can estimate the human brain activity without attaching any sensors that require preprocessing before attachment such as the brain wave electrodes and probes.

(2) ACQUISITION METHOD OF FACIAL-SURFACE PHOTOGRAPHED IMAGE DATA, AND ANALYSIS METHOD OF FACIAL-SURFACE PHOTOGRAPHED IMAGE DATA

Figure 1A:
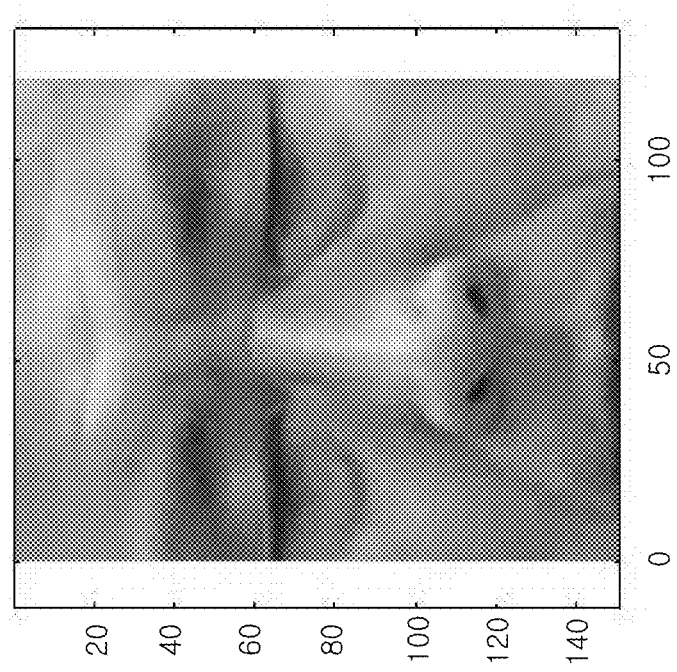
FIG. 1A is a diagram showing an example of the photographed image data.
Figure 2A:
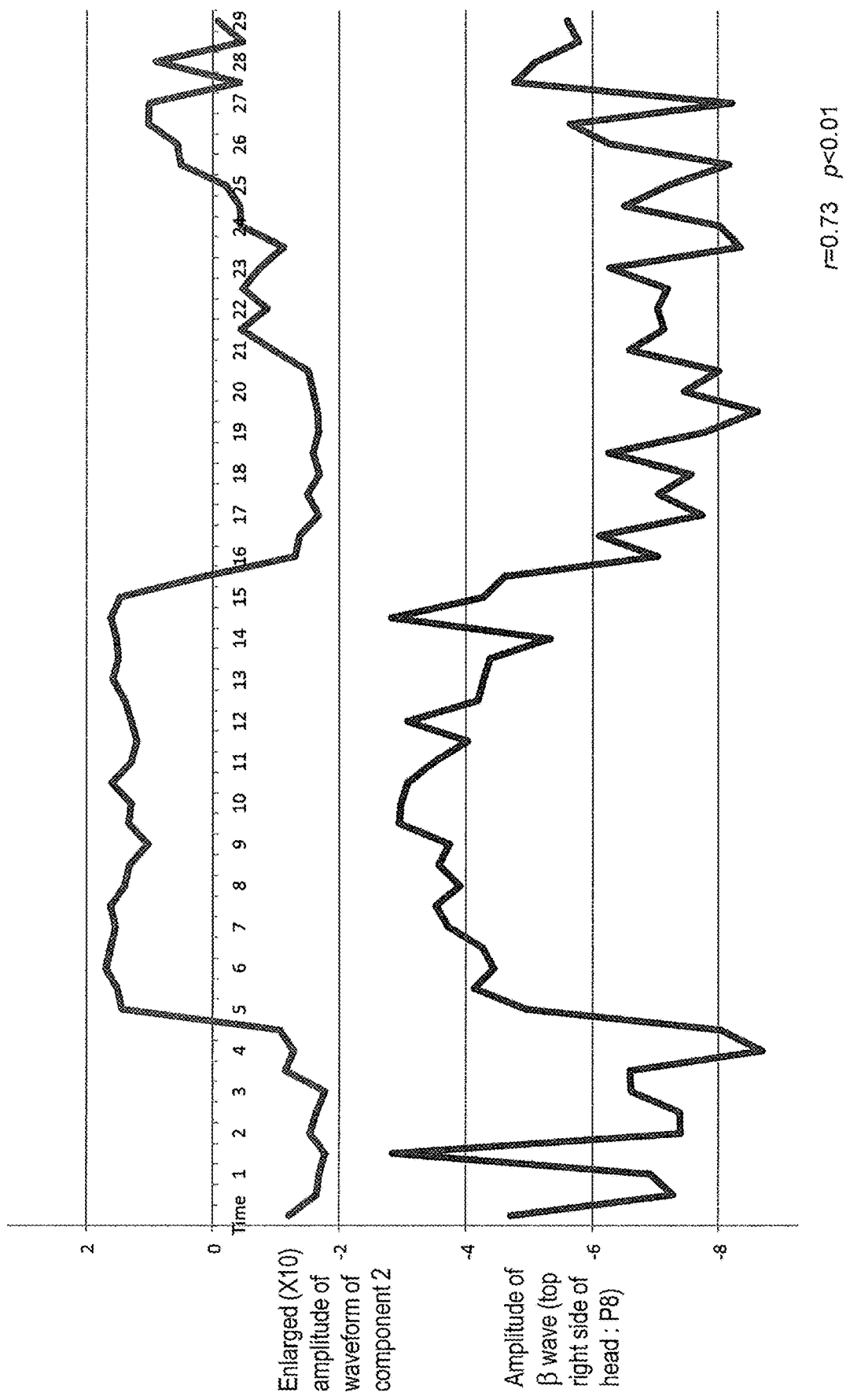
FIG. 2A is a diagram showing some of the results of an analysis of a component waveform based on the photographed image data on the facial surface of a test subject 1.
Figure 2B:
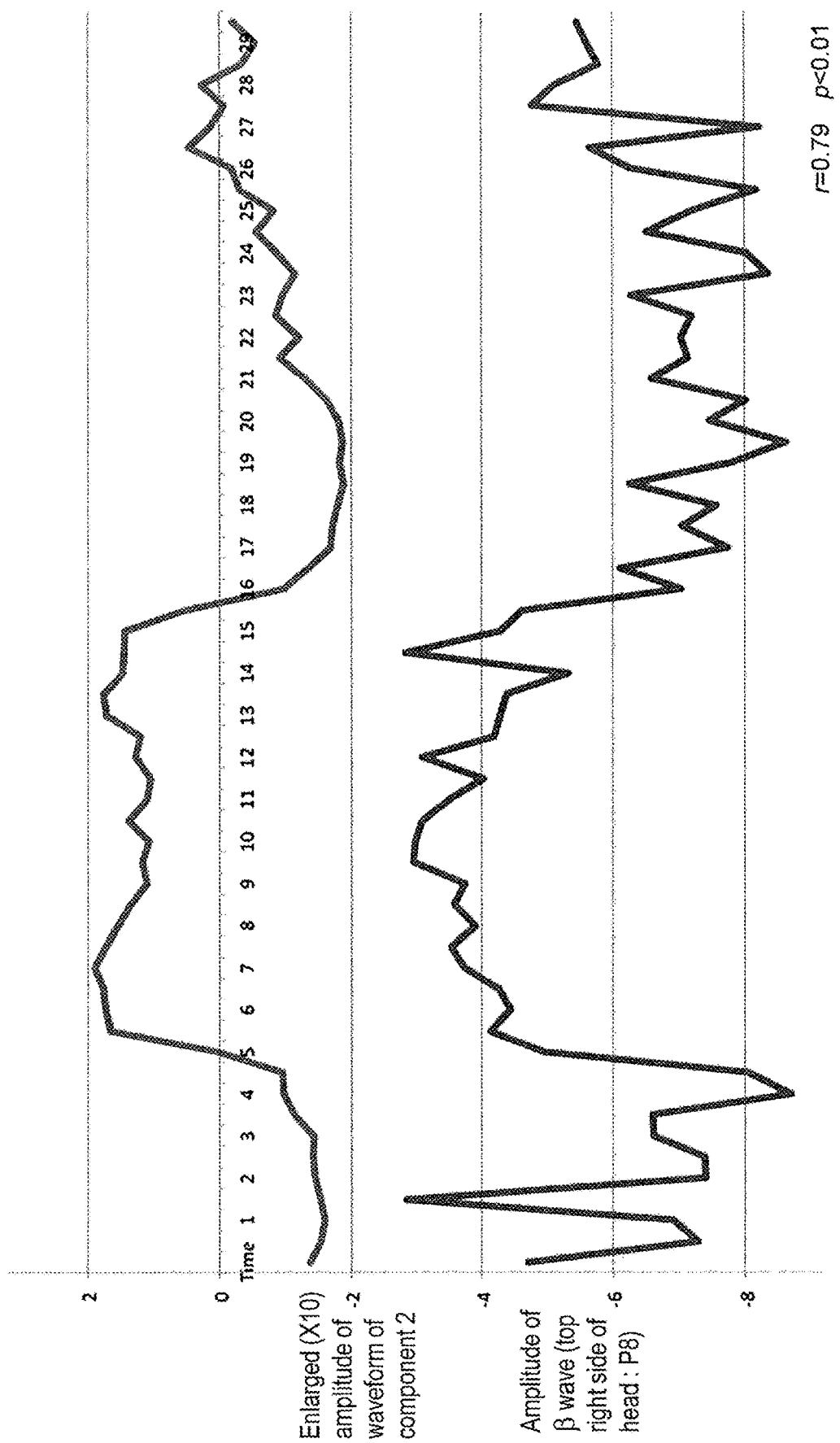
FIG. 2B is a diagram showing some of the results of an analysis of a component waveform based on facial skin temperature data on the test subject 1.
Figure 3A:
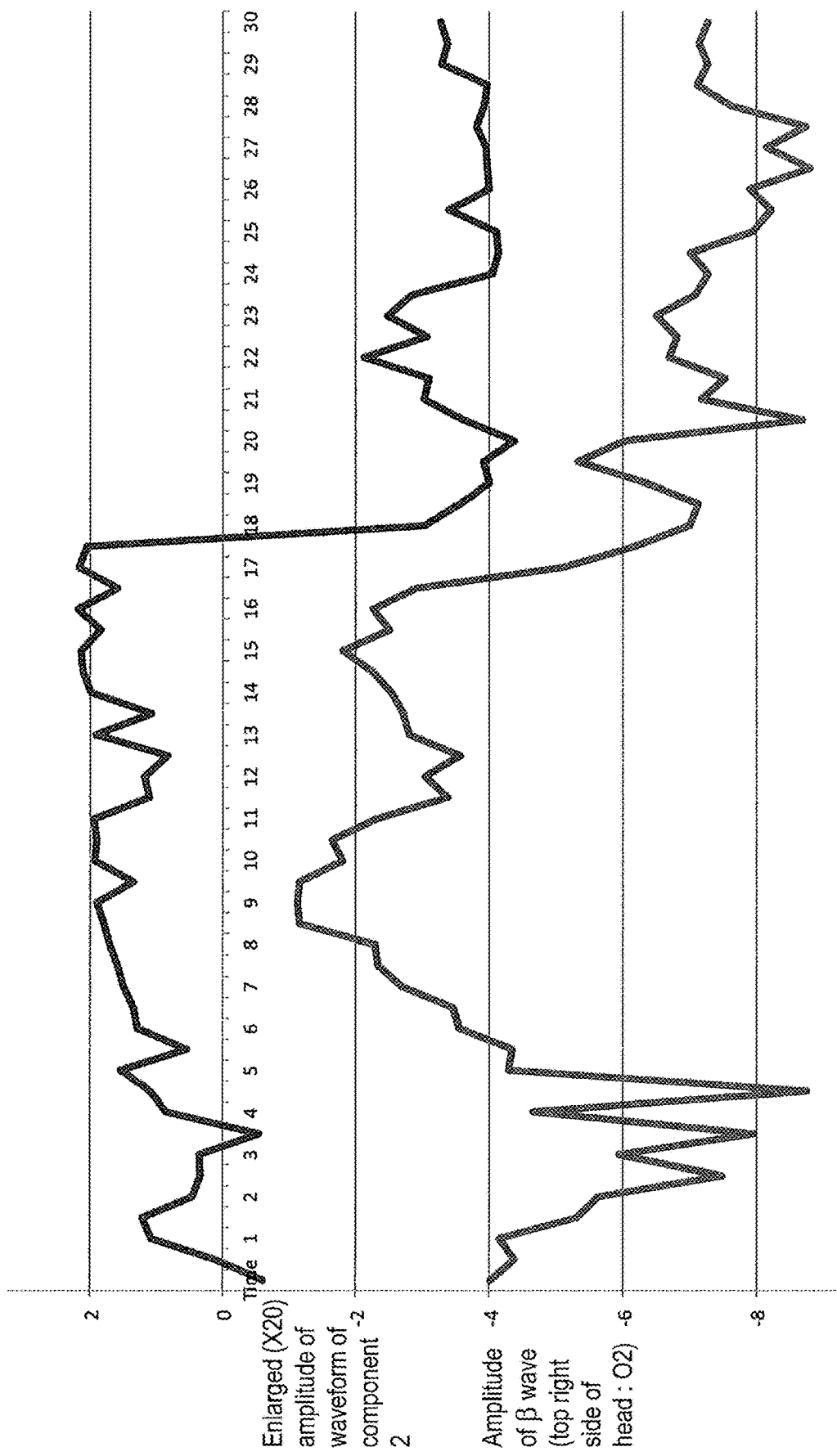
FIG. 3A is a diagram showing some of the results of an analysis of a component waveform based on the photographed image data on the facial surface of a test subject 2.
Figure 3B:
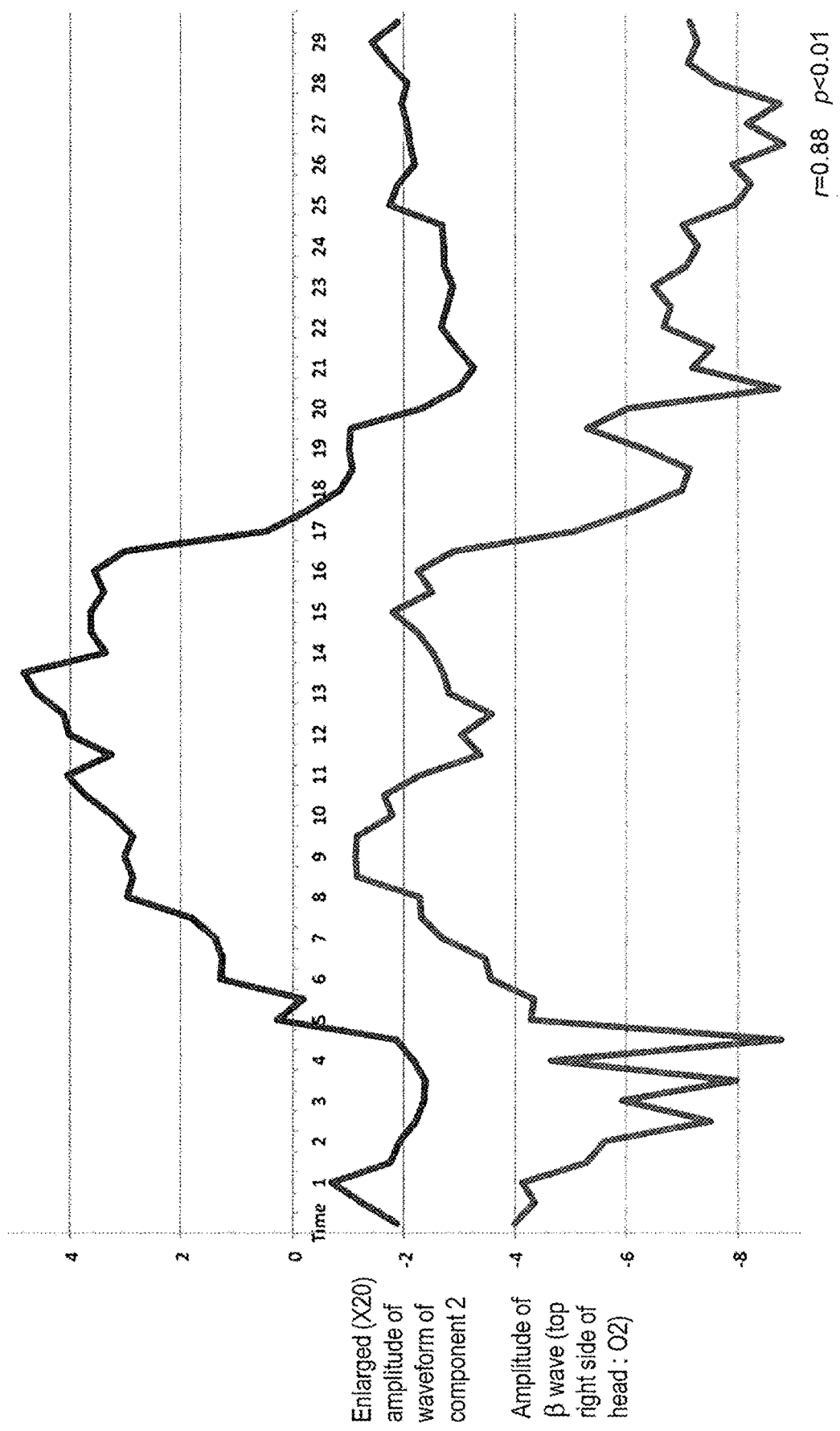
FIG. 3B is a diagram showing some of the results of an analysis of a component waveform based on the facial skin temperature data on the test subject 2.
Figure 4A:
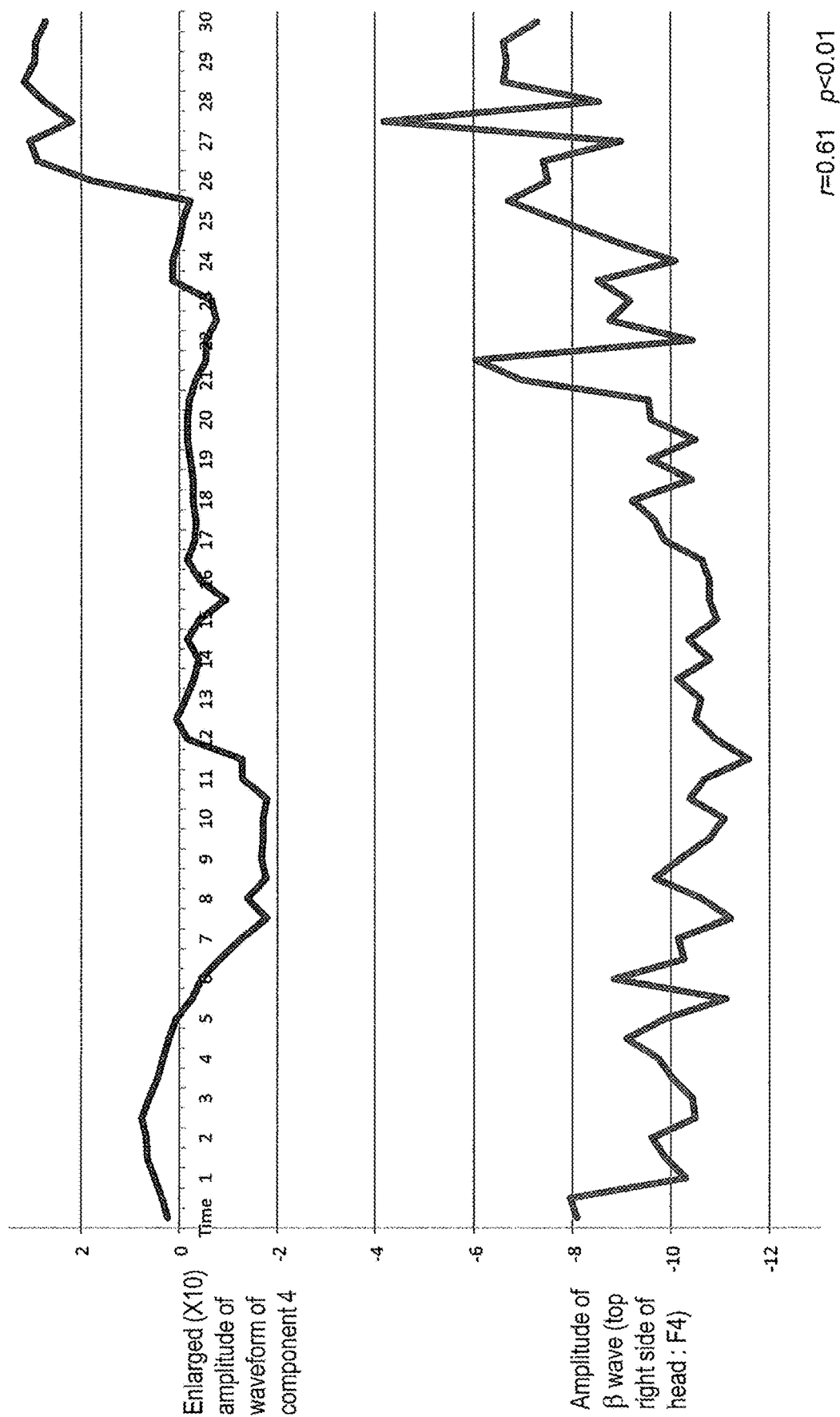
FIG. 4A is a diagram showing some of the results of an analysis of a component waveform based on the photographed image data on the facial surface of a test subject 3.
Figure 4B:
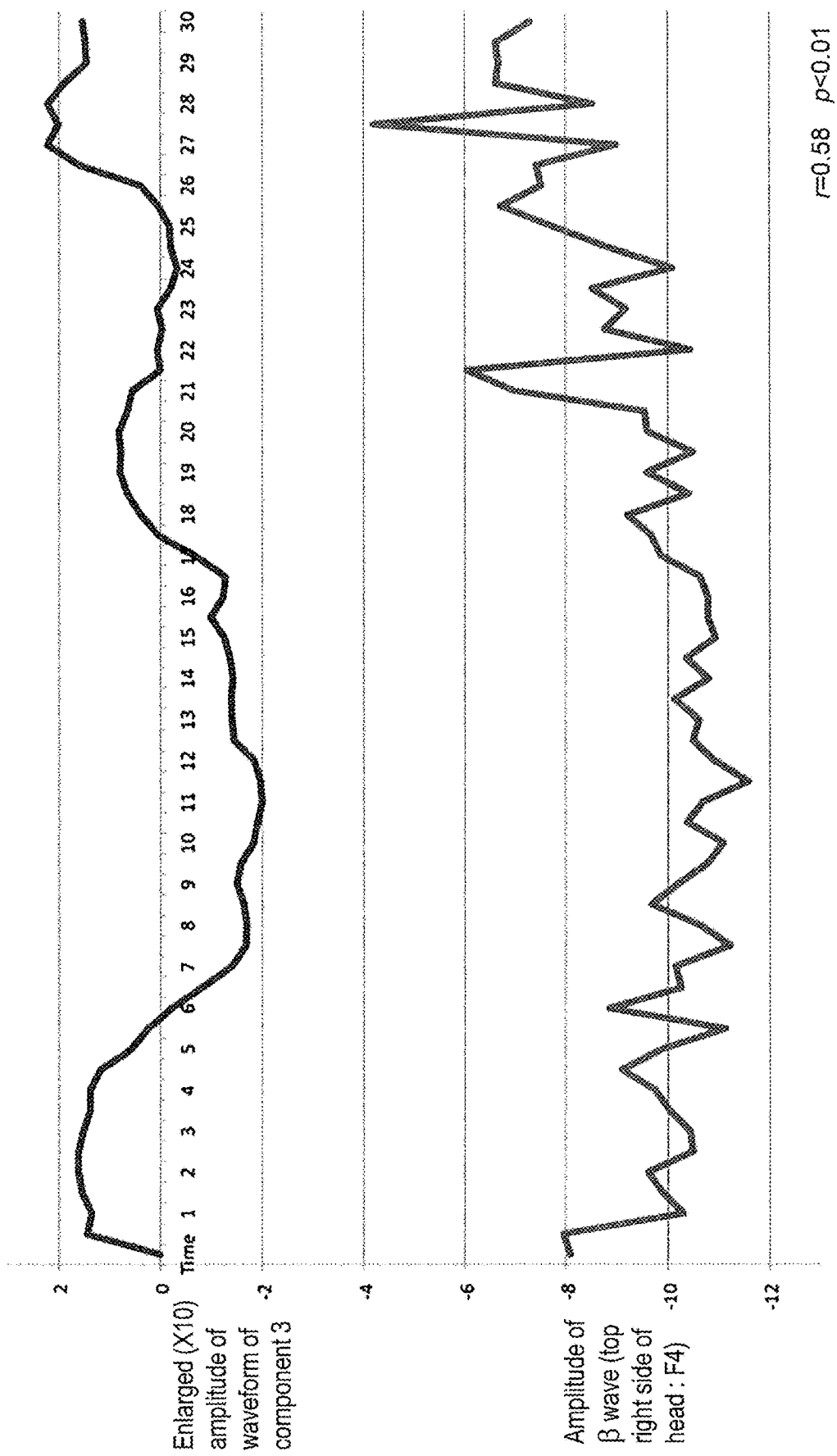
FIG. 4B is a diagram showing some of the results of an analysis of a component waveform based on the facial skin temperature data on the test subject 3.
Figure 5A:
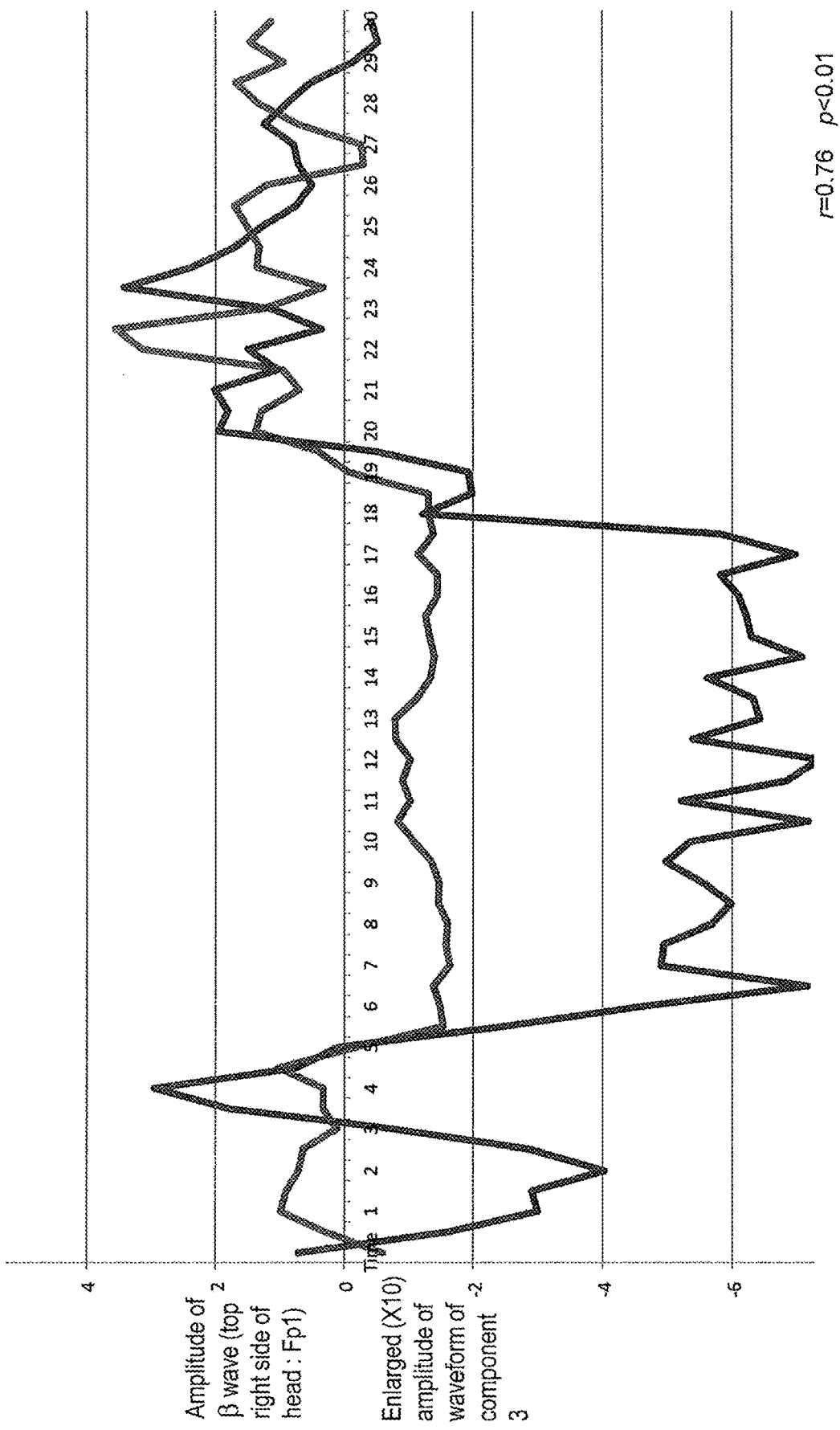
FIG. 5A is a diagram showing some of the results of an analysis of a component waveform based on the photographed image data on the facial surface of a test subject 4.
Figure 5B:
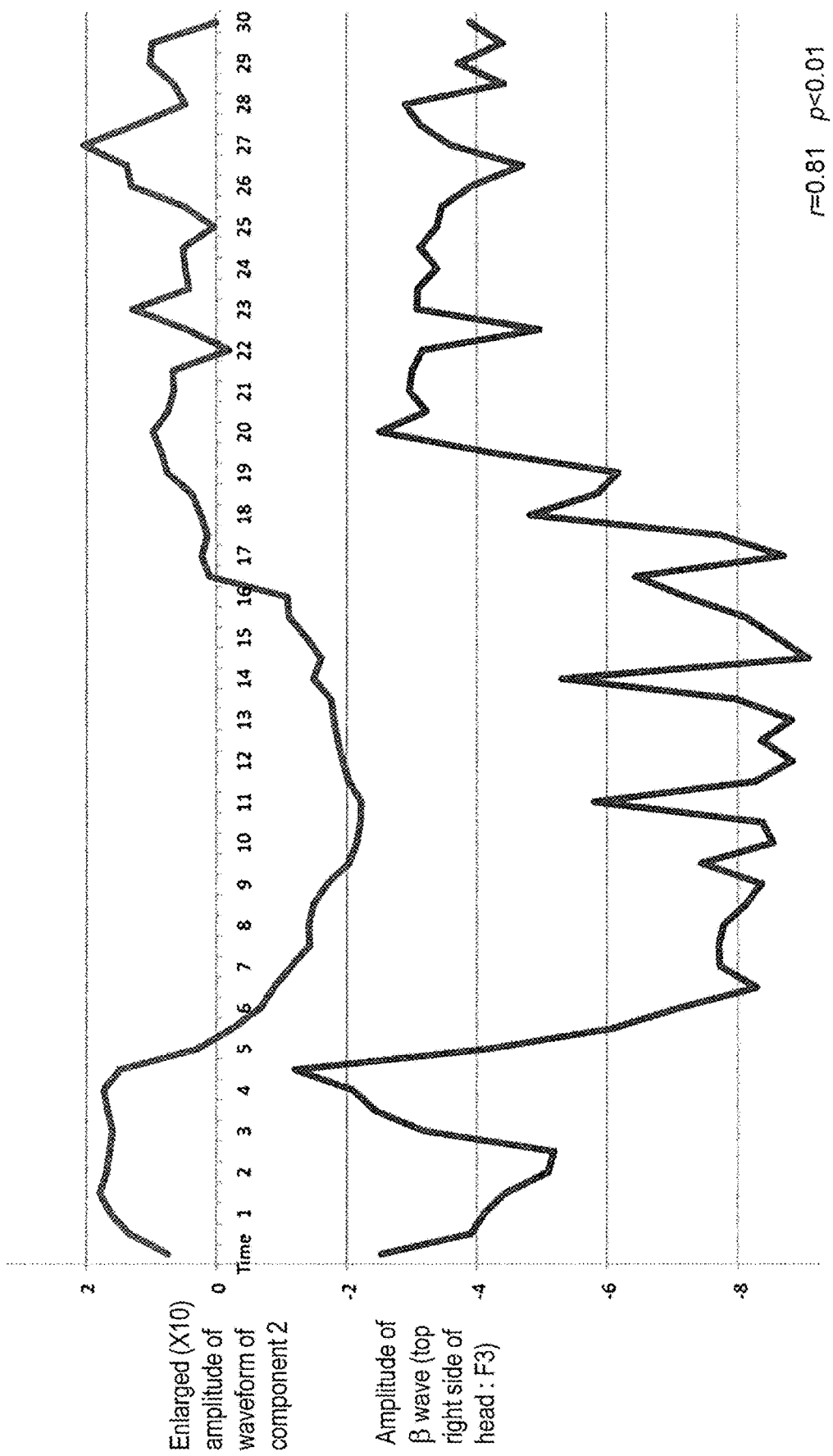
FIG. 5B is a diagram showing some of the results of an analysis of a component waveform based on the facial skin temperature data on the test subject 4.
Figure 6A:
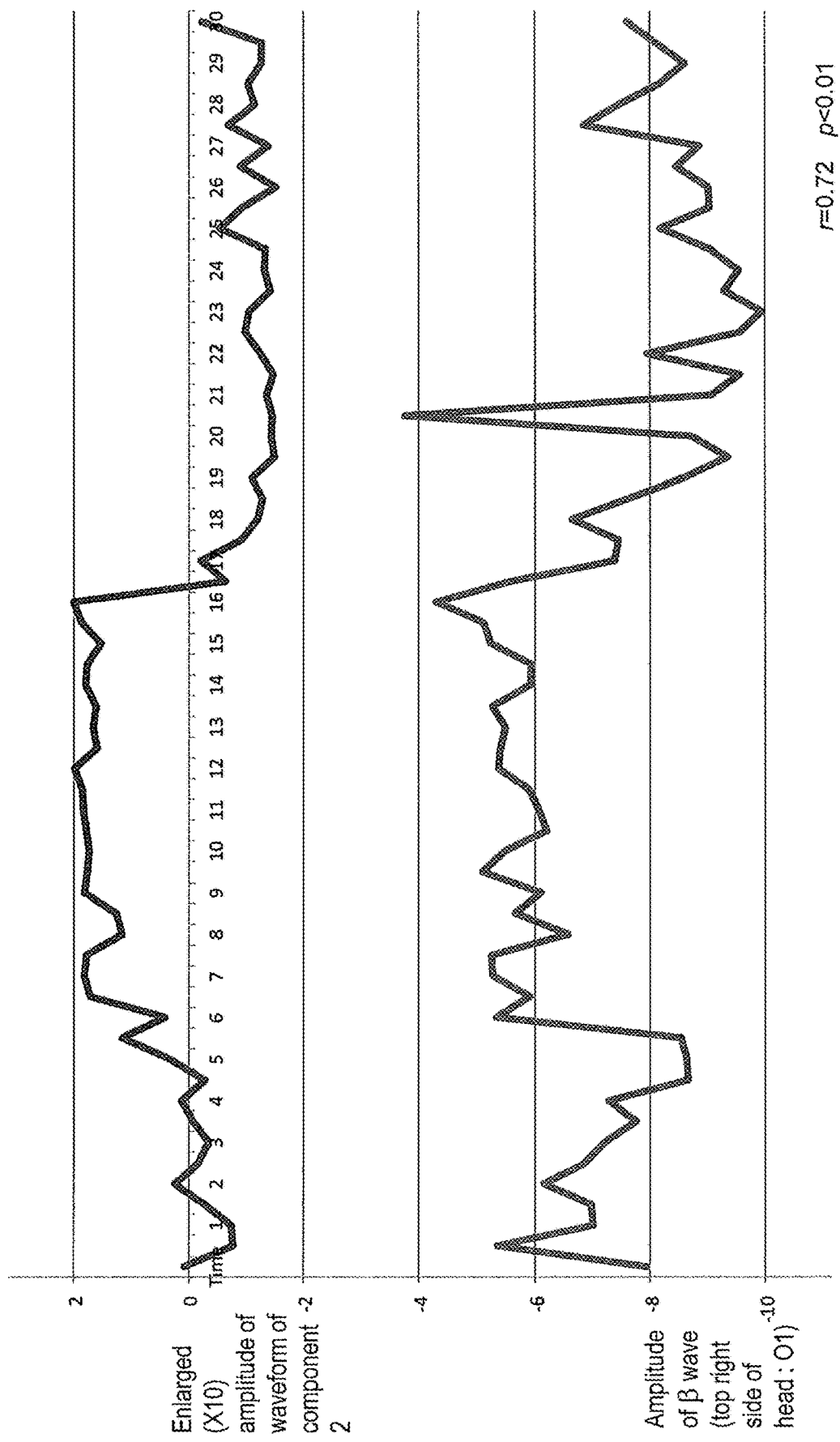
FIG. 6A is a diagram showing some of the results of an analysis of a component waveform based on the photographed image data on the facial surface of a test subject 5.
Figure 6B:
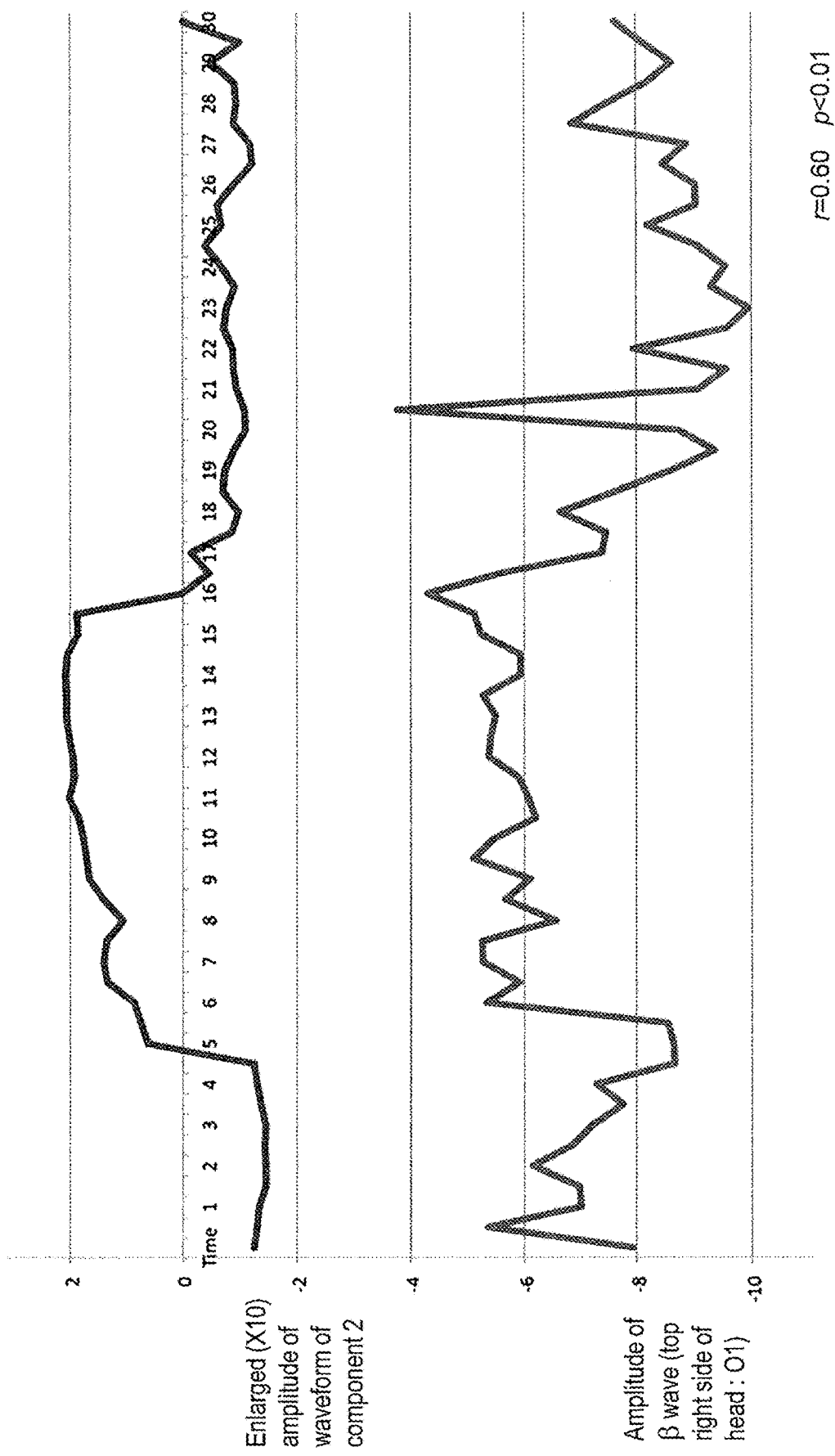
FIG. 6B is a diagram showing some of the results of an analysis of a component waveform based on the facial skin temperature data on the test subject 5.
Figure 7A:
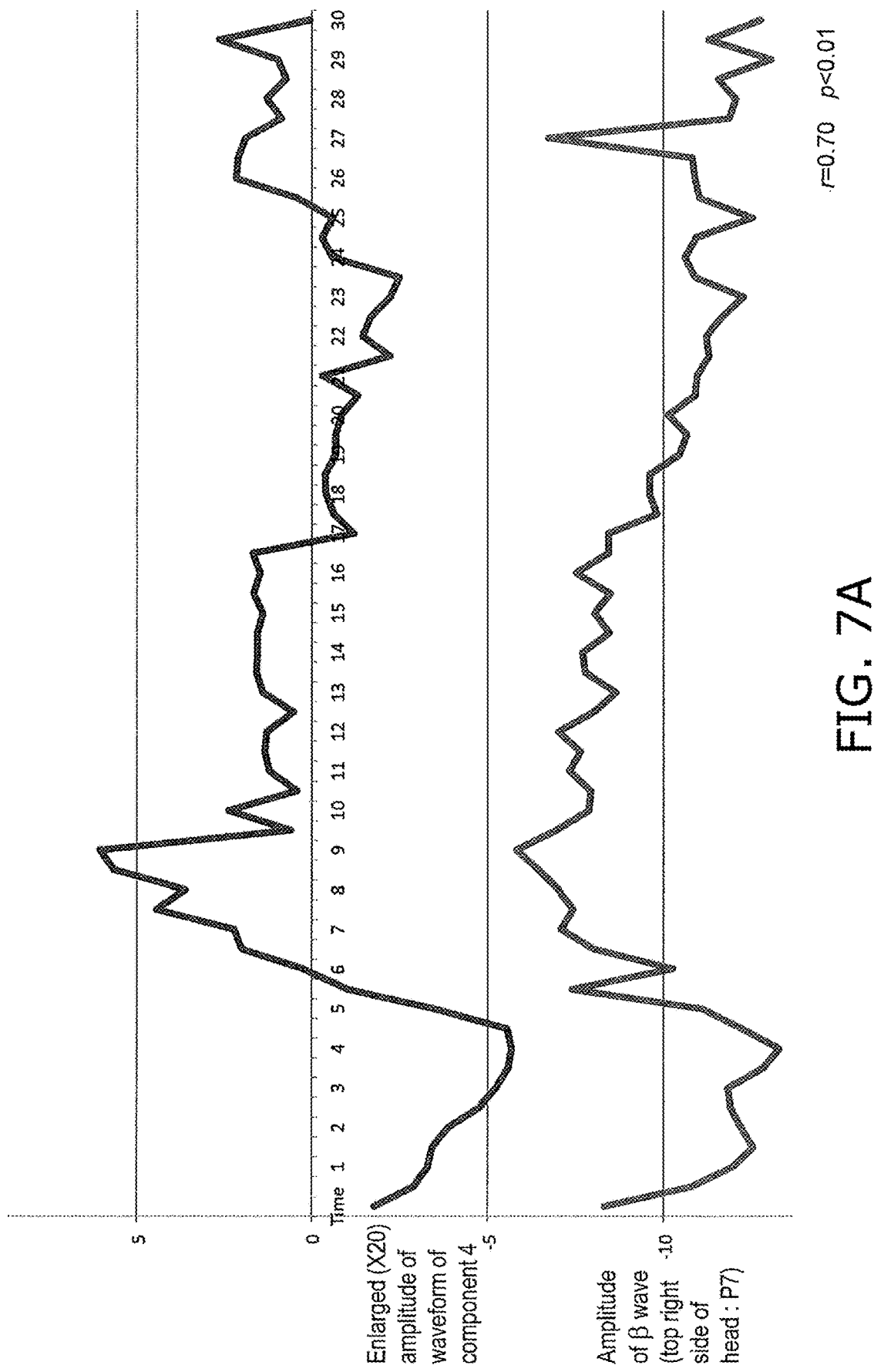
FIG. 7A is a diagram showing some of the results of an analysis of a component waveform based on the photographed image data on the facial surface of a test subject 6.
Figure 7B:
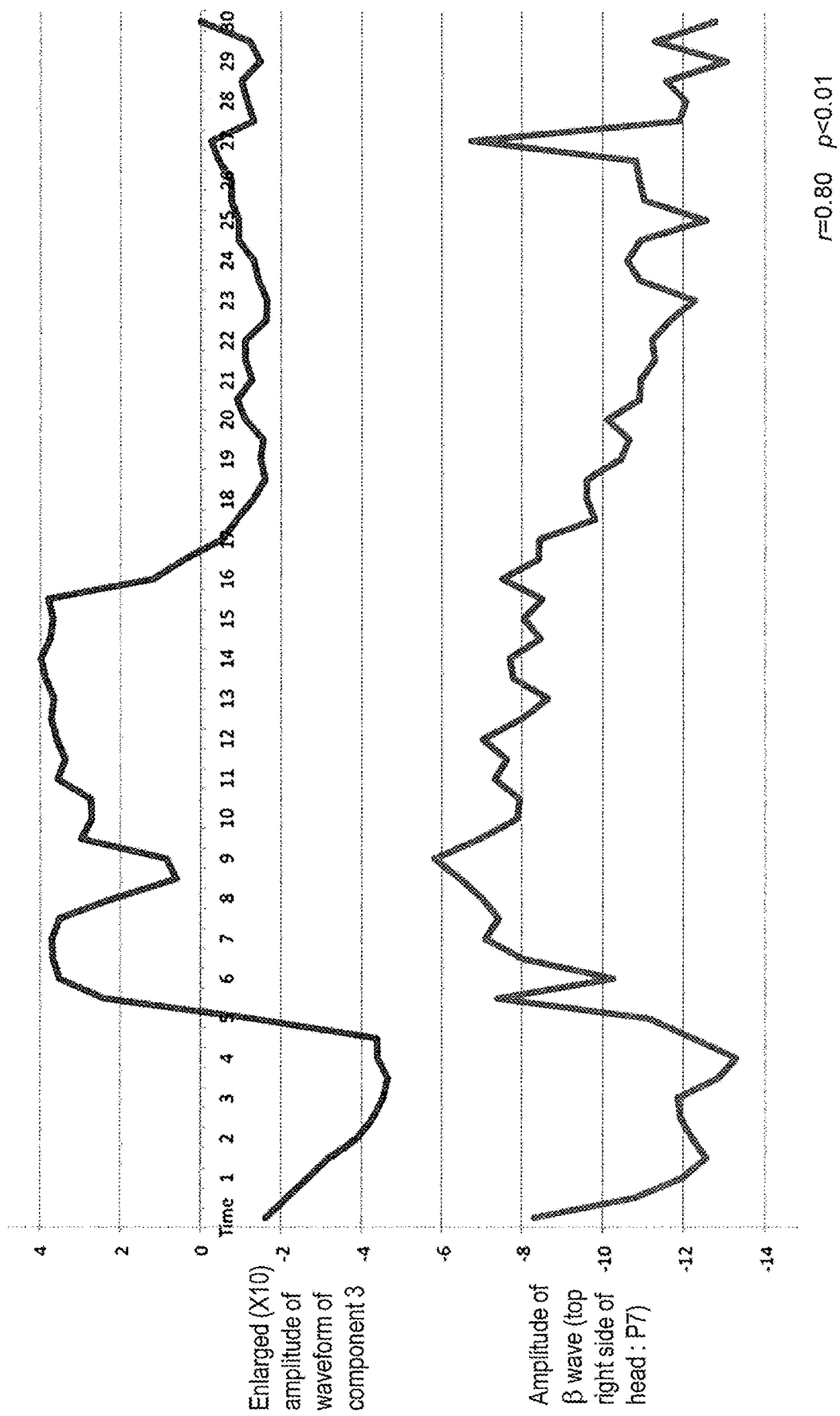
FIG. 7B is a diagram showing some of the results of an analysis of a component waveform based on the facial skin temperature data on the test subject 6.

FIG. 1A is a diagram showing an example of the photographed image data on the paranasal sinus peripheral region at the facial surface of a test subject photographed by a photographing device. FIG. 1B is a diagram showing an example of a blood-circulation-amount distribution diagram (image map).

Next, a description will be given on an acquisition method of the facial-surface photographed image data and an analysis method of the facial-surface photographed image data, both methods being used by the inventors to obtain the above-mentioned findings.

In the present test, the photographed image data was acquired from the facial surfaces of six test subjects. Specifically, these test subjects were seated on chairs in an artificial weather room that was kept at a room temperature of 25° C. Then, the photographed image data on the paranasal sinus peripheral region from the entire facial surface of each test subject was acquired in time series by using the photographing device capable of acquiring images in time series.

Here, brain has a mechanism called "Selective Brain Cooling System" to cool the brain independently of the body temperature. The selective brain cooling system is known to discharge heat generated by the brain activity using forehead or paranasal sinus peripheral region (including a part between eyes). Based on this fact, it is thought that a change in the blood-circulation-amount of the facial surface, which is considered to be proportional to the facial skin temperature that changes accompanied with the brain activity, appears at the forehead and/or the paranasal sinus peripheral region. From this viewpoint, the inventors considered that the brain activity can be estimated with high accuracy as long as a change in the blood-circulation-amount in at least the forehead and/or the paranasal sinus peripheral region of the facial surface can be captured. Accordingly, in the present test, the photographed image data on the paranasal sinus peripheral region at the facial surface of each test subject was acquired in time series.

Further, in the present test, the photographing device on the liquid crystal display side of an iPad Air (registered trademark) manufactured by Apple Inc. was used as the photographing device to obtain color moving image data as the time-series photographed image data. The photographing device was placed at a position located in front of the test subjects and spaced apart from the test subjects by 1.0 m. Then, the moving image data on the facial surface was obtained by continuously capturing the photographed image data with the photographing device for 30 minutes in photographing cycles of 30 frames/sec along the time axis.

Furthermore, in the present test, a brain function activation task was given to the test subject while the moving image data on the facial surface was being acquired. In this way, the moving image data on the facial surface at a brain resting time, as well as the moving image data on the facial surface at a brain activated time were acquired.

Here, the brain function activation tasks include psychological works done by the test subject based on a picture displayed on a display device or the like: such as calculation, recognition of numerical values, shape, and color, and memorization of marks, characters, and languages. In the present test, "mental arithmetic of multiplication" was adopted as the brain function activation task to make the test subjects calculate numerical characters displayed on the display device in longhand and input the answers on a keyboard. Note that in the present test, the brain function activation task was continuously given to the test subjects for ten minutes after five minutes have elapsed since the start of acquiring moving the image data on the facial surface.

In the analysis of the moving image data on the facial surface, the blood-circulation-amount data was calculated based on the RGB data acquired from the moving image data on the photographed facial surface, and then the calculated time-series blood-circulation-amount data was subjected to a singular value decomposition by using the Singular Value Decomposition (SVD) of MATLAB (registered trademark) as an analysis tool. Here, an erythema index "a*" that correlates with skin redness and hemoglobin amount was computed and determined from the RGB data on the image, in accordance with the CIE-L*a*b* color system. This erythema index was defined as the "blood-circulation-amount data." In the singular value decomposition, the blood-circulation-amount data (here, the erythema indexes) based on the RGB data acquired from all moving image data (data for 30 minutes) which was acquired in time series was defined as the target, the factor was defined as time data acquired every 30 seconds (60 time points for 30 minutes), and the measure was defined as the erythema index computed from the RGB data for the period of time (every 30 seconds) (erythema index that was computed by taking out frame data for one second every 30 seconds and acquiring an average of RGB values from the respective frame data: 240×320 pixels). By the singular value decomposition, the time-series blood-circulation-amount data based on the RGB data acquired from the moving image data on the facial surface was decomposed into a plurality of components, and then a time distribution V and a space distribution U of each of the components and a singular value S indicative of the size of each component were calculated. Note that the relationship between these can be given by the formula below:

$$X = (U*S)*V'$$  <Formula 1> where V' is a matrix configured by interchanging columns and rows of V.

Then, the time distribution V and the space distribution U of each component determined by the singular value decomposition were plotted in graphs to make a component waveform diagram and a blood-circulation-amount distribution diagram of each component.

Further, the thus-made component waveform diagram and blood-circulation-amount distribution diagram of each component were analyzed to identify a component which exhibited a change in the blood-circulation-amount of the facial surface that reflected the brain activity, i.e., an RGB change of the facial surface.

Regarding the component waveform diagram of each component, analysis was conducted to determine the presence or absence of the correlation between the amplitude of the component waveform and each of the brain resting time and the brain activated time. Specifically, it was evaluated whether or not there was a correlation between the amplitude shown in the component waveform diagram of each component and the rest period/activation period of the brain. In the present test, during the period of time when the photographed image data on the facial surface was being acquired, the brain resting time was defined as a period of time with no brain function activation task given to the test subjects. In the present test, the brain resting time was a period of five minutes from the start of data acquisition and a period of 15 minutes from when 15 minutes had elapsed since the start of data acquisition to the end of data acquisition. The brain activated time was defined as a period of time with the brain function activation task given to the test subjects. In the present test, the brain activated time was a period of ten minutes from the time when five minutes had elapsed since the start of data acquisition to the time when ten minutes had elapsed since then. Then, evaluation was performed on the presence or absence of the correlation between the amplitude of each component shown in the component waveform diagram and each of the brain resting time and the brain activated time. It is noted that the presence or absence of the correlation was determined by a statistical correlation analysis: when a significance level ($\alpha$) was 0.01 or less, it was determined that there was the correlation.

Regarding the blood-circulation-amount distribution diagram of each component, analysis was conducted on the presence or absence of a change in the blood-circulation-amount at a predetermined position of the facial surface. The blood-circulation-amount distribution diagram was made by arranging the space distributions U calculated every pixel, at the respective positions of the pixels. In the blood-circulation-amount distribution diagram for each component made in this way, it was evaluated whether or not there was any change in the blood-circulation-amount at the paranasal sinus peripheral region and the forehead. It is noted that the presence or absence of the change in the blood-circulation-amount at the paranasal sinus peripheral region and the forehead in the blood-circulation-amount distribution diagram was determined on the basis of the presence or absence of the change in the blood-circulation-amount that was observed through visual inspection, or the fact that the value of the blood-circulation-amount at the paranasal sinus peripheral region and the forehead shown in FIG. 1(b) was not "0.000."

It is noted that a polarity (plus or minus) of the blood-circulation-amount data X is determined depending on the relationship between the values of the space distribution U, the singular value S, and the time distribution V. Because of this, the polarity appears to be inversed in the component waveform diagram and the blood-circulation-amount distribution diagram of each component in some cases. Thus, in the evaluation of the component waveform diagram and the blood-circulation-amount distribution diagram, the polarity was not set as an evaluation target.

Further, to verify the correlation between the facial skin temperature and the blood-circulation-amount of the facial surface, while the photographed image data on the facial surface was acquired from the six test subjects in time-series. The facial skin temperature data was also acquired in time-series by an infrared thermography device. Then, the acquired facial skin temperature data was also subjected to the singular value decomposition by using the SVD of MATLAB (registered trademark) as the analysis tool and the component waveform diagram for each component was made according to the singular values S. The diagram was analyzed to determine the presence or absence of the correlation between the amplitude of the component waveform and each of the brain resting time and the brain activated time. The infrared thermography device used for the above processing is a device capable of detecting infrared radiant energy emitted from the target with an infrared camera, converting the detected infrared radiant energy into the temperature of a surface of the target (here, temperature in Celsius), and then displaying and storing the temperature distribution of converted temperatures as the facial skin temperature data (for example, image data representing the temperature distribution). Note that in this test, the infrared thermography device in use was an infrared camera R300 manufactured by NEC Avio Infrared Technologies Co., Ltd. The infrared camera was placed in front of the test subjects and spaced apart from the test subjects by 1.5 m.

In a case where the photographed image data on the facial surface is acquired by using the photographing device, if sunlight or the like hits the face during photographing, the light is reflected by the face. The reflected light occasionally enters a lens of the photographing device in some cases. As a result, the photographed image data on the photographed facial surface would have the reflected light recorded therein. Here, in the RGB data obtained from the photographed image data, a change in brightness based on the blood-circulation-amount of the facial surface is smaller than a change in brightness based on the reflected light. Because of this, if the blood-circulation-amount calculated based on the RGB data obtained from the photographed image data with the reflected light recorded therein is analyzed, it is considered that the RGB change (which is so-called noise) of the facial surface, which is unrelated to the brain activity, could be mixed in the data. For this reason, in order to prevent such mixing of the RGB change of the facial surface that is unrelated to the brain activity, relative blood-circulation-amount data was made from relative RGB data obtained by setting an average of all RGB data taken every 30 seconds at "0". Then, the thus-made blood-circulation-amount data was also subjected to the singular value decomposition by using the SVD of MATLAB (registered trademark) as the analysis tool and the component waveform diagram and the blood-circulation-amount distribution diagram for each component was made according to the singular values S. Then, the diagrams were analyzed to identify the component which exhibited the RGB change of the facial surface that reflects the brain activity.

Noted that for convenience of explanation, hereinafter, the relative blood-circulation-amount data based on the relative RGB data obtained by setting an average of all RGB data taken every predetermined time (every 30 seconds in the present test) at "0" is referred to as "relative-conversion blood-circulation-amount data", whereas the blood-circulation-amount data based on the RGB data provided before the conversion into the relative RGB data is simply referred to as "blood-circulation-amount data."

Furthermore, while the time-series photographed image data on the facial surface was acquired from the six test subjects by the photographing device, the brain wave of each test subject was measured by connecting electrodes to the scalp of the test subject to also evaluate the correlation between the amplitude of β wave (brain wave at a frequency of 13 to 30 Hz) known as the waveform appearing when brain cells were active, such as during waking, and the amplitude shown in the component waveform diagram. It is noted that in measurement of the brain waves, the electrodes were placed on 19 scalp locations (Fp1, Fp2, F3, F4, C3, C4, P3, P4, O1, O2, F7, F8, T3, T4, T5, T6, Fz, Cz, and Pz) based on the International 10-20 system.

Further, while the brain function activation task is given to the test subject, it is considered that the head of the test subject can move vertically. Consequently, the position of the facial surface of the test subject relative to the photographing device will change. For this reason, to verify whether or not a change in the position of the facial surface affects the RGB change of the facial surface, a contrast test was conducted on one test subject. In the contrast test, the time-series photographed image data on the facial surface of the test subject was acquired by using the photographing device as in the above-mentioned test. In addition, while no brain function activation task was given (i.e., at the brain resting time), the test subject was assigned to do a work of pressing a keyboard at random timings. With regard to the time-series blood-circulation-amount data based on the RGB data also, which was acquired from the time-series photographed image data on the facial surface obtained by photographing in the contrast test, the singular value decomposition was also conducted by using the SVD of MATLAB (registered trademark) as the analysis tool, and the component waveform diagram for each component was made according to the singular values S. Then, analysis was conducted to determine the presence or absence of the correlation between the amplitude of its component waveform and each of the brain resting time and the brain activated time. Furthermore, analysis was conducted to determine the presence or absence of the correlation between the amplitude of each component waveform and an actual movement of the facial surface. The actual movement of the facial surface was evaluated by acquiring a two-dimensional coordinate of a point corresponding to an actual point at the face, from the photographed image data and calculating a movement distance of the facial surface every 30 seconds during photographing on the basis of the photographed image data at the start of the contrast test. Further, the presence or absence of the correlation between the amplitude of each component waveform and the number of inputs to the keyboard during photographing was also analyzed. The number of inputs on the keyboard during photographing was evaluated by calculating a simple moving average every 30 seconds of the time-series photographed image data.

(3) ANALYSIS RESULT OF PHOTOGRAPHED IMAGE DATA ON FACIAL SURFACE

FIGS. 2 to 7 are diagrams showing some of the results of analysis of the component waveform diagrams based on the photographed image data on the facial surface (blood-circulation-amount data) or the facial skin temperature data. FIG. 2A is a diagram showing the amplitude of a component waveform of a component 2 based on photographed image data concerning a test subject 1 and the amplitude of a β wave of the measured brain waves of the test subject 1. FIG. 2B is a diagram showing the amplitude of a component waveform of the component 2 based on facial skin temperature data concerning the test subject 1 and the amplitude of the β wave of the measured brain waves of the test subject 1. FIG. 3A is a diagram showing the amplitude of a component waveform of the component 2 based on photographed image data concerning a test subject 2 and the amplitude of a β wave of the measured brain waves of the test subject 2. FIG. 3B is a diagram showing the amplitude of a component waveform of the component 2 based on facial skin temperature data concerning the test subject 2 and the amplitude of the β wave of the measured brain waves of the test subject 2. FIG. 4A is a diagram showing the amplitude of a component waveform of a component 4 based on photographed image data concerning a test subject 3 and the amplitude of a β wave of the measured brain waves of the test subject 3. FIG. 4B is a diagram showing the amplitude of a component waveform of a component 3 based on facial skin temperature data concerning the test subject 3 and the amplitude of the β wave of the measured brain waves of the test subject 3. FIG. 5A is a diagram showing the amplitude of a component waveform of the component 3 based on photographed image data concerning a test subject 4 and the amplitude of β wave of the measured brain waves of the test subject 4. FIG. 5B is a diagram showing the amplitude of a component waveform of the component 2 based on facial skin temperature data concerning the test subject 4 and the amplitude of the β wave of the measured brain waves of the test subject 4. FIG. 6A is a diagram showing the amplitude of a component waveform of the component 2 based on photographed image data concerning a test subject 5 and the amplitude of β wave of the measured brain waves of the test subject 5. FIG. 6B is a diagram showing the amplitude of a component waveform of the component 2 based on facial skin temperature data concerning the test subject 5 and the amplitude of the β wave of the measured brain waves of the test subject 5. FIG. 7A is a diagram showing the amplitude of a component waveform of the component 4 based on photographed image data concerning a test subject 6 and the amplitude of a β wave of the measured brain waves of the test subject 6. FIG. 7B is a diagram showing the amplitude of a component waveform of the component 3 based on facial skin temperature data concerning the test subject 6 and the amplitude of the β wave of the measured brain waves of the test subject 6.

As shown in FIGS. 2 to 7, from the results of each component waveform and brain wave analysis, it was confirmed that there was a correlation between the facial skin temperature and the blood-circulation-amount of the facial surface. Note that in the analysis based on either the facial skin temperature data or the blood-circulation-amount of the facial surface, it was also confirmed that there was a significant correlation between the amplitude of each component waveform and the amplitude of the β wave of brain waves measured by the electrodes attached on the top or back of the head.

Table 1 below shows the results of analysis of the photographed image data on the facial surface for each test subject.

TABLE 1

| Test subject | Correlation in blood-circulation-amount data | | Correlation in relative-conversion blood-circulation-amount data | |
|---|---|---|---|---|
| | Component waveform | Distribution of blood-circulation-amount | Component waveform | Distribution of blood-circulation-amount |
| Test subject 1 | Component 2 | 0.72 | Component 1 | 0.59 |
| | | | Component 2 | 0.85 |
| Test subject 2 | Component 1 | 0.82 | Component 1 | 0.62 |
| | Component 2 | 0.82 | Component 2 | 0.60 |
| Test subject 3 | Component 2 | 0.33 | Component 2 | 0.45 |
| | Component 3 | 0.31 | Component 3 | 0.56 |
| | | | Component 4 | 0.56 |
| Test subject 4 | Component 1 | 0.57 | Component 1 | 0.66 |
| | Component 3 | 0.71 | Component 3 | 0.65 |
| Test subject 5 | Component 1 | 0.56 | Component 1 | 0.51 |
| | Component 2 | 0.72 | Component 2 | 0.83 |
| Test subject 6 | Component 2 | 0.38 | Component 2 | 0.45 |
| | Component 4 | 0.68 | Component 3 | 0.51 |
| | | | Component 5 | 0.36 |

As shown in Table 1, from the results obtained by analysis of the above-mentioned photographed image data on the facial surface, it was confirmed that there was a significant correlation between the human brain activity and the components 1, 2, 3, 4, and 5 from among the plurality of components obtained through decomposition by the singular value decomposition of the time-series blood-circulation-amount data based on the photographed image data on the face surface. Note that here, not only the components having the significant correlation based on the blood-circulation-amount data and the significant correlation based on the relative-conversion blood-circulation-amount data, but also the components not exhibiting the significant correlation based on the blood-circulation-amount data while having the significant correlation based on the relative-conversion blood-circulation-amount data was determined to have the significant correlation with the human brain activity.

Table 2 below shows the results of the contrast test.

TABLE 2

| | |
|---|---|
| Component having a correlation with brain resting time/brain activated time | Component 1, Component 2 |
| Component having a correlation with movement distance of facial surface | Component 1, Component 3, Component 4 |
| Component having a correlation with the number of inputs to keyboard | Component 8 |

As shown in Table 2, in a case where the test subject moved in the contrast test while the photographed image data on the facial surface was being acquired, the component 2 among components had a significant correlation between the amplitude of its component waveform and each of the brain resting time and the brain activated time. However, the component 2 was not found to have any significant correlation between each of the movement distance and the number of inputs to the keyboard. From this fact, it was confirmed that, among a plurality of components that were obtained by conducting the singular value decomposition on the blood-circulation-amount data based on the RGB data acquired from the photographed image data on the facial surface, a component having a significant correlation with the brain activity could be influenced by the movement of the test subject while the time-series photographed image data on the facial surface was being acquired, but this influence was much smaller than the influence by the brain activity of the brain (influence due to the activation or rest of the brain).

From these results, the inventors have obtained the following findings.

The blood-circulation-amount data obtained from the RGB data on the facial surface, which was based on the time-series photographed image data on the facial surface acquired from the test subject, was decomposed into a plurality of components by the singular value decomposition, and the respective decomposed components were analyzed. As a result, the components 1, 2, 3, 4, and 5 were found to be those related to the brain activity, among the plurality of components. That is, the results revealed that, when the blood-circulation-amount data obtained from the RGB data on a facial surface which is based on the time-series photographed image data on the facial surface is decomposed into a plurality of components by the singular value decomposition; components that have a correlation with rest/activation of the brain are extracted from the decomposed plurality of components; and the extracted components are analyzed, the components exhibiting the RGB change of the facial surface that reflects the brain activity can be identified from the plurality of components. From this fact, the inventors have obtained the finding that human brain activity can be estimated based on the time-series photographed image data on the human's facial surface.

(4) BRAIN ACTIVITY ESTIMATION DEVICE 10

Next, based on the findings described above, a brain activity estimation device 10 according to an embodiment of the present invention that has been completed by the inventors of the present invention will be described. The brain activity estimation device 10 according to the present invention is not limited to the following embodiments, and various modifications can be made without departing from the gist of the present invention as appropriate.

Figure 8:
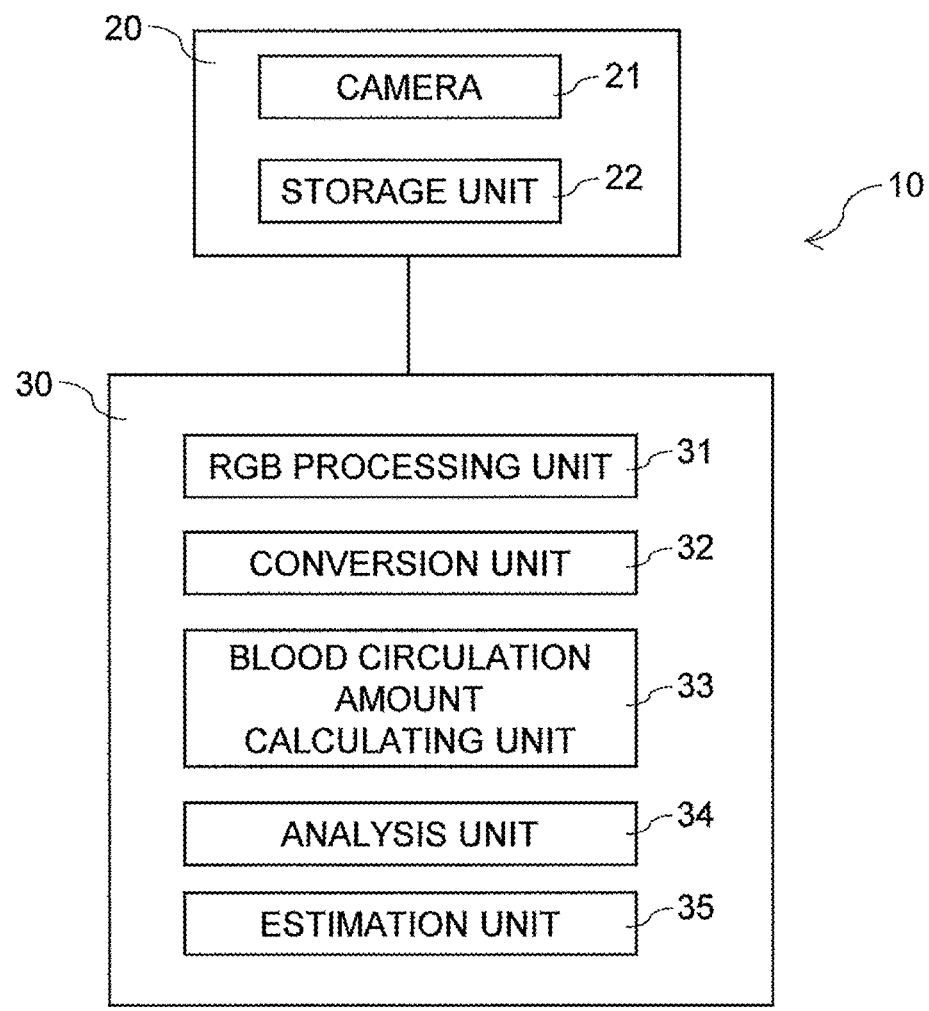
FIG. 8 is a schematic diagram of the brain activity estimation device according to one embodiment of the present invention.
Figure 9:
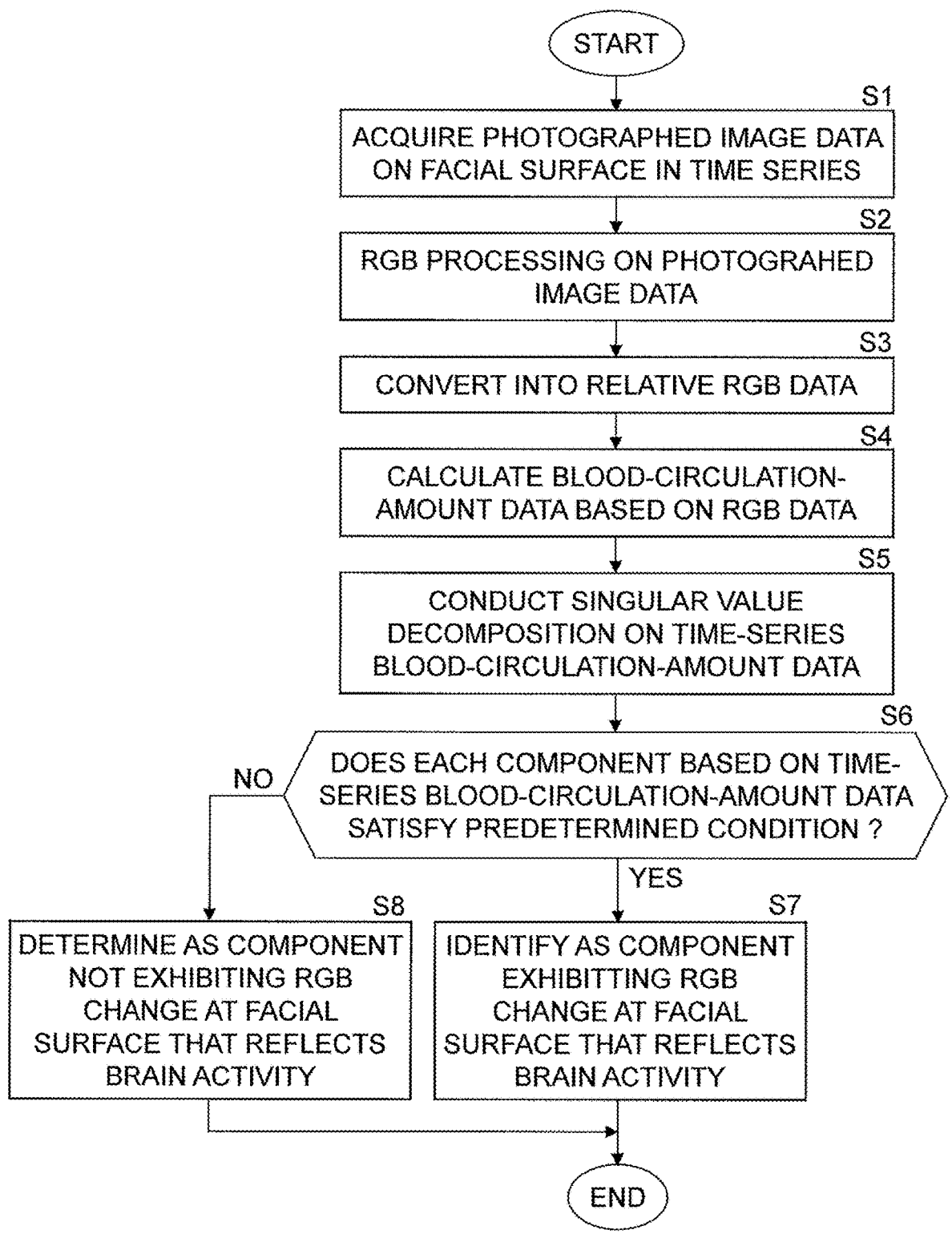
FIG. 9 is a flowchart showing an example of the flow of processing conducted when the brain activity estimation device identifies components which exhibit an RGB change of the facial surface that reflects a brain function.

FIG. 8 is a schematic diagram of the brain activity estimation device 10 according to the embodiment of the present invention. FIG. 9 is a flowchart showing an example of the flow of processing conducted when the brain activity estimation device 10 identifies a component exhibiting the RGB change of a facial surface that reflects a brain function.

The brain activity estimation device 10 is a device for estimating the brain activity of a person (test subject) from the photographed image data on the person's facial surface. As shown in FIG. 8, the brain activity estimation device 10 includes an image data acquisition portion or means 20 and a brain activity estimation portion or means 30.

The image data acquisition means 20 obtains photographed image data of at least a part of the person's facial surface in time series (step S1). It is noted that the image data acquisition means 20 is not particularly limited as long as it includes at least a photographing device. Examples of the image data acquisition means 20 include a portable terminal with a built-in photographing device, such as a smartphone and a tablet (e.g., iPad: registered trademark). Here, as shown in FIG. 8, the image data acquisition means 20 includes a camera 21 serving as a photographing device and a storage unit 22. The camera 21 is to acquire the photographed image data of a person's facial surface in time series. In this embodiment, the camera 21 photographs a moving image of a person's entire facial surface to acquire photographed moving image data. The storage unit 22 stores therein the time-series photographed image data captured by a photographing device. Here, the storage unit 22 stores moving image data acquired by the camera 21.

Note that in the present embodiment, the moving image of an entire facial surface is photographed by the camera 21, but is not limited thereto. A moving image including an image of at least the forehead and/or paranasal sinus peripheral region of a facial surface may be photographed.

In the present embodiment, a brain function activation task has been given to a person for a certain period of time while the time-series photographed image data on the facial surface is acquired by the image data acquisition means 20. That is, the photographed image data acquired by the image data acquisition means 20 includes data concerning the period of time during which the brain function activation task is being given to the person. It is noted that the brain function activation task given to a person is not limited particularly as long as it can be expected to make the brain activated. For example, the content of the brain function activation task may be determined as appropriate, according to the purpose of use of the brain activity estimation device 10.

The brain activity estimation means 30 estimates the human brain activity based on the time-series photographed image data on the facial surface that is acquired by the image data acquisition means 20. Specifically, as shown in FIG. 8, the brain activity estimation means 30 includes an RGB processing unit 31, a conversion unit 32, a blood-circulation-amount calculating unit 33, an analysis unit 34, and an estimation unit 35. It is noted that FIG. 8 shows an embodiment in which the brain activity estimation means 30 exists as one device that includes the RGB processing unit 31, the conversion unit 32, the blood-circulation-amount calculating unit 33, the analysis unit 34, and the estimation unit 35. However, the present invention is not limited thereto, and parts or each of the RGB processor unit 31, the conversion unit 32, the blood-circulation-amount calculating unit 33, the analysis unit 34, and the estimation unit 35 may be independent from one another.

The RGB processing unit 31 conducts the RGB processing on the photographed image data acquired by the image data acquisition means 20 to decompose the data into three color components, namely, an R component, a G component, and a B component (step S2). Here, the RGB processing may be conducted on the photographed image data on the entire facial surface. However, in the present embodiment, in order to reduce the amount of computation processing and noise, data on the forehead and/or the paranasal sinus peripheral region is extracted from the photographed image data, so that the RGB processing is conducted only on the extracted data.

The conversion unit 32 converts the RGB data of the photographed image data obtained by the RGB processing into relative RGB data (step S3). Specifically, the conversion unit 32 converts the RGB data into the relative RGB data by setting the average of the RGB data obtained from the acquired photographed image data every predetermined time (e.g., 30 seconds) as a reference.

The blood-circulation-amount calculating unit 33 calculates time-series blood-circulation-amount data on the facial surface, based on the RGB data of the photographed image data obtained by the RGB processing (step S4).

The analysis unit 34 decomposes the time-series relative-conversion blood-circulation-amount data into a plurality of components by a singular value decomposition, a principal component analysis, or an independent component analysis (step S5). In this embodiment, the analysis unit 34 conducts the singular value decomposition on the relative-conversion blood-circulation-amount data by using the SVD of MATLAB (registered trademark) as an analysis tool. Specifically, the singular value decomposition is performed, in which the time-series relative-conversion blood-circulation-amount data is defined as the target, the factor is defined as time data acquired at every predetermined time interval (for example, 30 seconds), and the measure is defined as the relative-conversion blood-circulation-amount data for each pixel that is computed from the relative RGB data at every predetermined time interval. The time-series relative-conversion blood-circulation-amount data is decomposed into a plurality of components by the singular value decomposition to calculate a time distribution, a space distribution, and a singular value indicative of the size of each component.

The analysis unit 34 determines whether or not each component satisfies a predetermined condition, in order to identify a component that exhibits the RGB change of the facial surface reflecting the brain activity, from the plurality of components decomposed by the singular value decomposition (step S6). Here, examples of the predetermined condition include a condition in which the amplitude of the component waveform of the component decomposed by the singular value decomposition has correlations with the changes of the brain at the brain resting time and a brain activated time (hereinafter referred to as a first condition), and a condition in which there is a change in the blood circulation amount at a predetermined part of the human facial surface with regard to the component decomposed by the singular value decomposition (hereinafter referred to as a second condition). The predetermined condition based on which the determination is made by the analysis unit 34 may include one or more set conditions. Here, the first condition is set as the predetermined condition.

The analysis unit 34 extracts, as a determination component, a component satisfying the predetermined condition, among the plurality of components. Further, the analysis unit 34 identifies a component satisfying all of the conditions included in the predetermined condition among the extracted determination components, as a component exhibiting the RGB change of the facial surface that reflects the brain activity (step S7). Meanwhile, the analysis unit 34 determines that the component determined not to satisfy at least one requirement included in the predetermined condition among the plurality of components is not a component exhibiting the RGB change of the facial surface that reflects the brain activity (step S8).

In the present embodiment, only one condition (first condition) is set as the predetermined condition as mentioned above, and there is a certain period of time during which the brain function activation task is given to the person while the time-series photographed image data on the facial surface is being acquired. Thus, the analysis unit 34 conducts an analysis by comparing the component waveform of each component with the period of time during which the brain function activation task is given to the person and the period of time during which the task is not given to the person. The period of time during which no brain function activation task is given is defined as a brain resting time, whereas the period of time during which the brain function activation task is given is defined as a brain activated time. By using the result of the comparison analysis based on the component waveform data, the analysis unit 34 evaluates whether or not the component waveform of each component has any correlation with the brain resting time and the brain activated time. Then, the analysis unit 34 extracts a component evaluated to have the correlation, from among the plurality of components, as a determination component satisfying the predetermined condition, and identifies the component as the component exhibiting the RGB change of the facial surface that reflects the brain activity. Meanwhile, the analysis unit 34 determines that the components evaluated not to have any correlation among the plurality of components do not satisfy the predetermined condition and are not the components that exhibit the RGB change of the facial surface reflecting the human brain activity.

Here, in the present embodiment, the brain function activation task is given to the person for a certain period of time when the time-series photographed image data on the facial surface is acquired. Based on this data, the analysis unit 34 extracts the determination component, but the content of the first condition, i.e., the extraction means of the determination component in the analysis unit 34 is not limited thereto. For example, in a case where the component exhibiting the component waveform that has correlations with the brain resting time and the brain activated time is already specified by previous experiments or the like among from the plurality of components, the analysis unit 34 extracts the specified component as the determination component from the plurality of components. When some human body motions that are known to be related to the activation/rest of brains, such as eye movement or blink, are also detected by the brain activity estimation device 10, the analysis unit 34 may extract a determination component from the plurality of components, by analyzing and evaluating through comparison between the detected result and the component waveform of each component. Note that the reference for the analysis unit 34 to determine whether or not the first condition is satisfied is appropriately determined by simulation, an experiment, working on paper, or the like, according to the purpose of use or the like of the brain activity estimation device 10.

When the second condition is set as the predetermined condition, the analysis unit 34 extracts the determination component based on the presence or absence of a change in the blood-circulation-amount of the facial surface at a predetermined part of the human facial surface. Specifically, the analysis unit 34 determines whether or not a change in the blood-circulation-amount occurs at the paranasal sinus peripheral region and/or forehead, based on the blood-circulation-amount distribution diagram, depending on the plurality of components decomposed by the singular value decomposition. When the change in the blood-circulation-amount occurs, the analysis unit 34 determines the component of interest satisfies the second condition. Meanwhile, when no change in the blood-circulation-amount occurs at the paranasal sinus peripheral region and/or forehead, the analysis unit 34 determines that the component of interest does not satisfy the second condition. Note that the reference for the analysis unit 34 to determine whether or not the second condition is satisfied is appropriately determined by simulation, an experiment, working on paper, or the like, according to the purpose of use or the like of the brain activity estimation device 10.

Further, when the time-series blood-circulation-amount data based on the RGB data prior to the conversion into the relative RGB data is calculated by the blood-circulation-amount calculating unit 33, also regarding the plurality of components obtained by the singular value decomposition of the blood-circulation-amount data or the like, the analysis unit 34 may determine whether or not the above-mentioned first condition and/or second condition are satisfied, and may extract a determination component.

The estimation unit 35 estimates the human brain activity based on the component identified in the analysis unit 34 as the component that exhibits the RGB change of the facial surface reflecting the human brain activity. Specifically, the estimation unit 35 estimates whether the person's brain is in an active state or in an inactive state when the photographed image data of the facial surface is acquired, based on the component waveform data of the component identified by the analysis unit 34.

With this configuration, the brain activity estimation device 10 can estimate human brain activity based on the time-series photographed image data on the facial surface. The estimated result by the estimation unit 35 is displayed on display means (not shown) such as a display, so that whether the person's brain is in the active state or in the inactive state can be notified.

In a case where after the analysis unit 34 identifies the component exhibiting the RGB change of the facial surface that reflects the brain activity, and then the image data acquisition means 20 acquires the time-series photographed image data on the facial surface, the brain activity estimation device 10 may decompose the acquired photographed image data on the facial surface into a plurality of components by the singular value decomposition, and analyze only the identified component to estimate whether or not the person's brain was in the active state or in the inactive state when the photographed image data on the facial surface was acquired. Such a brain activity estimation device 10 can be used to control equipment and devices such as air conditioners to create an interior environment appropriate for the person.

(5) CHARACTERISTICS (5-1)

To estimate a human brain activity, when data detected by any method selected from electroencephalography, functional magnetic resonance imaging, and near infrared spectroscopy is utilized, in many cases, sensors that require preprocessing before attaching such as brain wave electrodes and probes need be used, or the measurement place has some constraint. Further, because the devices used by these detecting methods are very expensive, in an attempt to manufacture a brain activity estimation apparatus equipped with such a device, the manufacturing cost would increase.

In the present embodiment, the human brain activity is estimated based on the time-series photographed image data on the facial surface acquired by the image data acquisition means 20. Because of this, the human brain activity can be estimated without attaching any sensors requiring the preprocessing before attachment such as brain wave electrodes and probes. Therefore, the human brain activity can be easily estimated, compared to the case using a conventional detection method, such as electroencephalography, functional magnetic resonance imaging, and near infrared spectroscopy.

The present embodiment only needs to acquire the image data on at least a part of the facial surface and thereby can reduce manufacturing cost, compared to a brain activity estimation device equipped with the device used by the conventional detection method.

Further, the human brain activity can be also estimated based on the human's facial skin temperature data that can be acquired by using the thermography device. However, the thermography device generally costs about several tens of thousands of Japanese yen. For this reason, the brain activity estimation device that achieves more reduction in manufacturing cost than the use of the thermography device is expected. In the present embodiment, the low-cost photographing device is employed as the image data acquisition means 20, so that the manufacturing cost can be reduced more than when the thermography device is employed.

Existing research sites have adopted an average value approach in which an average of all temperature data included in the time-series facial skin temperature data is calculated, and the facial skin temperature data corresponding to the calculated average is analyzed, thereby estimating the human brain activity. However, the facial skin temperature data includes noise in addition to the components actually reflecting the brain activity, and when the temperature data of a part of the body is analyzed, the influence by noise becomes relatively large, whereby the average value approach cannot estimate the brain activity precisely. For this reason, the inventors have conceived of a component analysis approach in which the time-series facial skin temperature data is decomposed into the plurality of components by a singular value decomposition, a principal component analysis, or an independent component analysis, and a component related to the brain activity is identified from the decomposed plurality of components. In the component analysis approach, all temperature data is decomposed, thereby making it possible to remove any component including noise. As a result, this component analysis approach can precisely estimate the brain activity, compared to the average value approach.

In addition, the inventors have considered that the component analysis approach could be also effective even when the brain activity is estimated from the time-series data on the blood-circulation-amount of the facial surface which is proportional to the facial skin temperature. For this reason, the inventors have adopted the component analysis approach in which the time-series blood-circulation-amount data based on the RGB data obtained from the time-series facial surface image data is decomposed into the plurality of components by a singular value decomposition, a principal component analysis, or an independent component analysis, and a component related to the brain activity is identified from the decomposed plurality of components. In the brain activity estimation device 10 of the present embodiment, the time-series blood-circulation-amount data based on the RGB data obtained from the time-series facial surface image data is decomposed into the plurality of components by the singular value decomposition, and the brain activity is estimated from the decomposed components. Thus, the component including noise can be removed, whereby the brain activity can be precisely estimated.

(5-2)

Here, in a case where the presence or absence of the brain function activation tasks actually given to a human brings the human brain into the activated state or the resting state when the time-series image data on the facial surface is acquired, there is a high possibility that the component having a correlation between its component waveform and each of the brain activated time and the brain resting time is a component exhibiting a change in the blood-circulation-amount that reflects the brain activity.

In the present embodiment, the brain function activation task is given to the person for a certain period of time while the time-series image data on the facial surface is acquired by the image data acquisition means 20. That is, in this embodiment, the presence or absence of the brain function activation tasks actually given to a person creates a situation which brings the human brain into the activated state or the resting state. The time-series blood-circulation-amount data based on the RGB data obtained from the image data acquired in this way is decomposed into a plurality of components by the singular value decomposition, and the correlation between its component waveform and each of the brain activated time and the brain resting time is evaluated for each component. Then, the component having the correlation is extracted from the plurality of components as the determination component. This can reduce the probability of extraction of the component, which is less related to the human brain activity, as the extraction component from a plurality of components, as compared to, for example, when a predetermined component previously specified by an experiment or the like is extracted as an extraction component from a plurality of components.

(5-3)

Here, brain has the mechanism called "Selective Brain Cooling System" to cool the brain independently of the body temperature. The selective brain cooling system is known to discharge heat generated by the brain activity using the forehead and the paranasal sinus peripheral region. This means, a change in the blood-circulation-amount of the facial surface, which has a correlation with the facial skin temperature according to a brain activity, appears at the forehead and/or the paranasal sinus peripheral region.

In the present embodiment, the blood-circulation-amount data based on the RGB data on the forehead and/or the paranasal sinus peripheral region is analyzed to extract the determination component. Thus, the component related to the human brain activity can be extracted with high accuracy.

In the present embodiment, an area for conducting the RGB processing and for acquiring the blood-circulation-amount data is limited to the forehead and/or the paranasal sinus peripheral region. Thus, the present embodiment can reduce the amount of computation processing, compared to the case the photographed image data on the entire facial surface is subjected to the RGB processing or the blood-circulation-amount data is calculated based on the data on the entire facial surface.

(5-4)

In a case where the photographed image data on the facial surface is acquired by using a photographing device, if sunlight or the like hits the face during photographing, the light is reflected by the face into a lens of the photographing device in some cases. As a result, the photographed image data on the photographed facial surface would have the reflected light recorded therein. Here, in the RGB data obtained from the photographed image data, a change in brightness based on the blood-circulation-amount of the facial surface is smaller than a change in brightness based on the reflected light. Because of this, if a blood-circulation-amount calculated based on the RGB data obtained from the photographed image data with the reflected light recorded therein is analyzed, an RGB change (which is so-called noise) of the facial surface that is not related to the brain activity could be mixed in the data.

In the present embodiment, the RGB data of the photographed image data obtained by the RGB processing is converted into the relative RGB data, to thereby calculate the time-series relative-conversion blood-circulation-amount data based on the relative RGB data. Due to the relative-conversion blood-circulation-amount data calculated in this way, a relative change in the RGB data on the facial surface can be captured every predetermined time.

Thus, the RGB change of the facial surface due to the external factor not related to the brain activity can be detected.

In the present embodiment, the time-series relative-conversion blood-circulation-amount data is decomposed into a plurality of components by the singular value decomposition, and each of the components is analyzed. Thus, the component including the RGB change of the facial surface due to the external factor not related to the brain activity can be removed as a noise component. In this way, the component related to the human brain activity can be identified with high accuracy.

(5-5)

When the blood-circulation-amount data obtained based on the RGB data provided before the conversion into the relative RGB data is analyzed, there exists a component that is not extracted as the one having a significant correlation. However, in some cases, this kind of component could be extracted as the one having a significant correlation when the relative-conversion blood-circulation-amount data obtained based on the relative RGB data is analyzed. In contrast, when the blood-circulation-amount data obtained based on the RGB data provided before the conversion into the relative RGB data is analyzed, there exists another component that is extracted as one that has a significant correlation. However, in some cases, that kind of component may not be extracted as the one having a significant correlation when the relative-conversion blood-circulation-amount data obtained based on the relative RGB data is analyzed. Here, there is a possibility that the RGB data provided before the conversion into the relative RGB data is influenced by external factors, such as light from the outside. The above-mentioned difference regarding the extracted components is considered to be related to the influence of the external factor. That is, it can be said that the relative-conversion blood-circulation-amount data obtained based on the relative RGB data is more important and more valid than the blood-circulation-amount data obtained based on the RGB data provided before the conversion into the relative RGB data.

In the present embodiment, only the relative-conversion blood-circulation-amount data obtained based on the relative RGB data is analyzed. Thus, the components related to the human brain activity can be identified with higher accuracy than in the case where only the blood-circulation-amount data obtained based on the RGB data provided before the conversion into the relative RGB data is analyzed. Further, this configuration can reduce the amount of computation processing, compared to the case where both of the blood-circulation-amount data obtained based on the RGB data provided before the conversion into the relative RGB data and the relative-conversion blood-circulation-amount data obtained based on the relative RGB data are analyzed.

(6) MODIFIED EXAMPLES (6-1) Modified Example A

As mentioned above, for example, a portable terminal with a built-in photographing device, such as a smartphone and a tablet (e.g., iPad: registered trademark) etc. can be utilized as the camera 21. That is, the above-mentioned photographed image data in use can be the one generated by photographing an image in the visible light region.

In this case, in the blood-circulation-amount calculating unit of the above-mentioned embodiment, the R components among the respective pixels in the RGB data may be mainly used to calculate the blood-circulation-amount data on the facial surface. Also, the blood-circulation-amount data is not necessarily limited to the erythema index as long as the blood-circulation-amount data can be calculated based on the RGB data.

(6-2) Modified Example B

In the above-mentioned embodiment, in step S4, the time-series blood-circulation-amount data on the facial surface is calculated based on the RGB data of the photographed image data obtained by the RGB processing. In other words, the blood-circulation-amount calculating unit 33 in the above-mentioned embodiment calculates the relative-conversion blood-circulation-amount data based on the relative RGB data converted by the conversion unit 32. However, instead of or in addition to this, the blood-circulation-amount data may be calculated based on the RGB data provided before the conversion into the relative RGB data. Here, the blood-circulation-amount data calculated based on the RGB data provided before the conversion into the relative RGB data is more likely to generate (or has a higher capability to verify) a component having a correlation with the brain activity. Thus, for example, the blood-circulation-amount data calculated based on the RGB data provided before the conversion into the relative RGB data may be analyzed prior to the relative-conversion blood-circulation-amount data calculated based on the relative RGB data. In addition, for example, first, the blood-circulation-amount data may be analyzed to extract the components having the significant correlation, and regarding the relative-conversion blood-circulation-amount data, only the components corresponding to the extracted components may be analyzed, whereby the amount of the computation processing can be reduced.

(6-3) Modified Example C

The above-mentioned camera 21 is a normal camera used in visible light region as a precondition, but can be an infrared camera. In this case, infrared light is irradiated, and its reflected light is used to produce a photographed image by the infrared camera. Consequently, the photographed image data concerning changes of the facial surface of a target person or the like can be obtained. The inventors of the present invention have confirmed that there is a correlation between the blood-circulation-amount data calculated from the photographed image data obtained by infrared reflection and the blood-circulation-amount data calculated by mainly using the R component of each pixel included in the RGB data produced by photographing in the visible light region. Therefore, through the use of the photographed image data obtained from the infrared reflection also, the human brain activity can be estimated.

(6-4) Modified Example D

Although in the above-mentioned description, the brain activity estimation device 10 includes the image data acquisition means 20 and the brain activity estimation means 30, the brain activity estimation device according to the present embodiment is not limited to such a form. That is, the brain activity estimation device according to the present embodiment may take any form for the other configuration as long as it includes the blood-circulation-amount calculating unit 33, the analysis unit 34, and the estimation unit 35. Specifically, the brain activity estimation device according to the present embodiment may take a form, including not only a form in which the device itself generates the image data by photographing, but also a form in which photographed image data is received from an external device to analyze it therein.

INDUSTRIAL APPLICABILITY

The present invention can easily estimate human brain activity, and thus is effective for application to devices that require the estimation of human brain activity.

What is claimed is:

1. A brain activity estimation device comprising:
   a data acquisition unit configured to acquire time-series data of RGB data on a facial surface of a subject; and
   a blood-circulation-amount calculating unit configured to calculate time-series blood-circulation-amount data on the facial surface of the subject based on the RGB data,
   an estimation unit configured to estimate brain activity of the subject based on the time-series data of the blood-circulation-amount data calculated by the blood-circulation-amount calculating unit,
   the time series data of RGB data including data in a period of time during which a brain function activation task is given, the brain function activation task being displayed on a display device.

2. The brain activity estimation device according to claim 1, wherein
   the estimation unit extracts a plurality of time distributions from the time-series data set of RGB data, and
   the estimation unit estimates the brain activity based on the extracted data.

3. The brain activity estimation device according to claim 1, wherein
   the estimation unit extracts a time distribution and a space distribution from the time-series data set of RGB data, and
   the estimation unit estimates the brain activity based on the extracted data.

4. The brain activity estimation device according to claim 1, wherein
   the estimation unit extracts a plurality of time distributions and a plurality of space distributions from the time-series data set of RGB data, and
   the estimation unit estimates the brain activity based on the extracted data.

5. The brain activity estimation device according to claim 1, wherein
   the estimation unit extracts a plurality of time distributions and a plurality of space distributions from the time-series data set of RGB data, and
   the estimation unit analyzes each time distribution and then analyzes the space distributions.

6. The brain activity estimation device according to claim 1, wherein
   the estimation unit estimates the brain activity based on RGB data of at least one of a paranasal sinus peripheral region and a forehead.

7. The brain activity estimation device according to claim 1, wherein
   the estimation unit
      decomposes the time-series of RGB data by singular value decomposition, principal component analysis, or independent component analysis,
      extracts a time distribution and a space distribution, and
      estimates the brain activity based on the extracted data.

8. The brain activity estimation device according to claim 1, wherein
   the estimation unit extracts a plurality of time distributions from the time-series data set of RGB data, and
   the estimation unit estimates the brain activity based on the extracted data.

9. The brain activity estimation device according to claim 8, wherein
   the estimation unit estimates the brain activity based on RGB data of at least one of a paranasal sinus peripheral region and a forehead.

10. The brain activity estimation device according to claim 1, wherein
    the estimation unit extracts a time distribution and a space distribution from the time-series data set of RGB data, and
    the estimation unit estimates the brain activity based on the extracted data.

11. The brain activity estimation device according to claim 10, wherein
    the estimation unit estimates the brain activity based on RGB data of at least one of a paranasal sinus peripheral region and a forehead.

12. The brain activity estimation device according to claim 1, wherein
    the estimation unit extracts a plurality of time distributions and a plurality of space distributions from the time-series data set of RGB data, and
    the estimation unit estimates the brain activity based on the extracted data.

13. The brain activity estimation device according to claim 12, wherein
    the estimation unit estimates the brain activity based on RGB data of at least one of a paranasal sinus peripheral region and a forehead.

14. The brain activity estimation device according to claim 1, wherein
    the estimation unit extracts a plurality of time distributions and a plurality of space distributions from the time-series data set of RGB data, and
    the estimation unit analyzes each time distribution and then analyzes the space distributions.

15. The brain activity estimation device according to claim 14, wherein
    the estimation unit estimates the brain activity based on RGB data of at least one of a paranasal sinus peripheral region and a forehead.

16. The brain activity estimation device according to claim 1, wherein
    the estimation unit estimates the brain activity based on RGB data of at least one of a paranasal sinus peripheral region and a forehead.

17. The brain activity estimation device according to claim 16, wherein
    the estimation unit
       decomposes the time-series of RGB data by singular value decomposition, principal component analysis, or independent component analysis,
       extracts a time distribution and a space distribution, and
       estimates the brain activity based on the extracted data.

18. The brain activity estimation device according to claim 1, wherein
    the estimation unit
       decomposes the time-series of RGB data by singular value decomposition, principal component analysis, or independent component analysis, extracts a time distribution and a space distribution, and estimates the brain activity based on the extracted data.

* * * * *